United States Patent
Silva et al.

(10) Patent No.: US 11,567,063 B2
(45) Date of Patent: Jan. 31, 2023

(54) METHODS FOR ASSESSING CELL VIABILITY OR PREDICTING CELL RESPONSE TO A TREATMENT USING CELL MOVEMENT

(71) Applicant: H. LEE MOFFITT CANCER CENTER AND RESEARCH INSTITUTE, INC., Tampa, FL (US)

(72) Inventors: Ariosto S. Silva, Tampa, FL (US); Zayar P. Khin, Tampa, FL (US)

(73) Assignee: H. LEE MOFFITT CANCER CENTER AND RESEARCH INSTITUTE, INC., Tampa, FL (US)

(*) Notice: Subject to any disclaimer, the term of this patent is extended or adjusted under 35 U.S.C. 154(b) by 245 days.

(21) Appl. No.: 15/036,951

(22) PCT Filed: Nov. 14, 2014

(86) PCT No.: PCT/US2014/065817
§ 371 (c)(1),
(2) Date: May 16, 2016

(87) PCT Pub. No.: WO2015/073908
PCT Pub. Date: May 21, 2015

(65) Prior Publication Data
US 2016/0258931 A1 Sep. 8, 2016

Related U.S. Application Data

(60) Provisional application No. 61/904,550, filed on Nov. 15, 2013.

(51) Int. Cl.
| | |
|---|---|
| *G01N 33/50* | (2006.01) |
| *G01N 15/14* | (2006.01) |
| *G01N 33/574* | (2006.01) |
| *C12M 1/34* | (2006.01) |
| *G01N 15/10* | (2006.01) |
| *G01N 21/76* | (2006.01) |
| *G01N 21/64* | (2006.01) |
| *A61B 10/02* | (2006.01) |

(52) U.S. Cl.
CPC ......... *G01N 33/5011* (2013.01); *C12M 41/46* (2013.01); *G01N 15/1475* (2013.01); *G01N 15/1484* (2013.01); *G01N 33/5047* (2013.01); *G01N 33/57426* (2013.01); *A61B 2010/0258* (2013.01); *G01N 21/6458* (2013.01); *G01N 21/763* (2013.01); *G01N 2015/1006* (2013.01); *G01N 2201/0221* (2013.01); *G01N 2800/52* (2013.01)

(58) Field of Classification Search
None
See application file for complete search history.

(56) References Cited

PUBLICATIONS

Perlman, Zachary E., et al. "Multidimensional drug profiling by automated microscopy." Science 306.5699 (2004): 1194-1198.*
Jeong, Kwan, John J. Turek, and David D. Nolte. "Volumetric motility-contrast imaging of tissue response to cytoskeletal anti-cancer drugs." Optics Express 15.21 (2007): 14057-14064.*
Choi, Bernard, et al. "The importance of long-term monitoring to evaluate the microvascular response to light-based therapies." The Journal of investigative dermatology 128.2 (2008): 485.*
Gjorevski, Nikolce, and Celeste M. Nelson. "Mapping of mechanical strains and stresses around quiescent engineered three-dimensional epithelial tissues." Biophysical journal 103.1 (2012): 152-162.*
Manji, Gulam A., and Paul D. Friesen. "Apoptosis in Motion: An Apical, P35-Insensitive Caspase Mediates Programmed Cell Death in Insect Cells* 210." Journal of Biological Chemistry 276.20 (2001): 16704-16710.*
Lemons, Johanna MS, et al. "Quiescent fibroblasts exhibit high metabolic activity." PLoS biology 8.10 (2010): e1000514.*
Bellamy WT, Dalton WS, Gleason MC, Grogan TM, Trent JM. Development and characterization of a melphalan-resistant human multiple myeloma cell line. Cancer Res 1991;51:995-1002.
Chmielecki J, Foo J, Oxnard GR, Hutchinson K, Ohashi K, Somwar R, et al. Optimization of dosing for EGFR-mutant non-small cell lung cancer with evolutionary cancer modeling. Sci Transl Med 2011;3:90ra59.
Chou TC. Theoretical basis, experimental design, and computerized simulation of synergism and antagonism in drug combination studies. Pharmacol Rev 2006;58:621-81.
Durie BG, Jacobson J, Barlogie B, Crowley J. Magnitude of response with myeloma frontline therapy does not predict outcome: importance of time to progression in southwest oncology group chemotherapy trials. J Clin Oncol 2004;22:1857-63.
Gardner SN, Fernandes M. New tools for cancer chemotherapy: computational assistance for tailoring treatments. Mol Cancer Ther 2003;2:1079-84.
Gardner SN. A mechanistic, predictive model of dose-response curves for cell cycle phase-specific and -nonspecific drugs. Cancer Res 2000;60:1417-25.
Harousseau JL, Attal M, Avet-Loiseau H. The role of complete response in multiple myeloma. Blood 2009;114:3139-46.
Hokanson JA, Brown BW, Thompson JR, Drewinko B, Alexanian R. Tumor growth patterns in multiple myeloma. Cancer 1977;39:1077-84.
International Search Report and Written Opinion, issued in International Application No. PCT/US2014/065817, dated Mar. 25, 2015.
Ishii T, Seike T, Nakashima T, Juliger S, Maharaj L, Soga S, et al. Anti-tumor activity against multiple myeloma by combination of KW-2478, an Hsp90 inhibitor, with bortezomib. Blood Cancer J 2012;2:e68.

(Continued)

*Primary Examiner* — G Steven Vanni
(74) *Attorney, Agent, or Firm* — Meunier Carlin & Curfman LLC

(57) ABSTRACT

Disclosed is a method for selecting a cancer treatment regimen for a subject.

16 Claims, 25 Drawing Sheets

(56) References Cited

PUBLICATIONS

Kirshner J, Thulien KJ, Martin LD, Debes Marun C, Reiman T, Belch AR, et al. A unique threedimensional model for evaluating the impact of therapy on multiple myeloma. Blood 2008;112:2935-45.

Landau DA, Carter SL, Stojanov P, McKenna A, Stevenson K, Lawrence MS, et al. Evolution and impact of subclonal mutations in chronic lymphocytic leukemia. Cell 2013;152:714-26.

Meads MB, Gatenby RA, Dalton WS. Environment-mediated drug resistance: a major contributor to minimal residual disease. Nat Rev Cancer 2009;9:665-74.

Meads MB, Hazlehurst LA, Dalton WS. The bone marrow microenvironment as a tumor sanctuary and contributor to drug resistance. Clin Cancer Res 2008;14:2519-26.

Misund K, Baranowska KA, Holien T, Rampa C, Klein DC, Borset M, et al. A method for measurement of drug sensitivity of myeloma cells co-cultured with bone marrow stromal cells. J Biomol Screen 2013;18:637-46.

Nair RR, Emmons MF, Cress AE, Argilagos RF, Lam K, Kerr WT, et al. HYD1-induced increase in reactive oxygen species leads to autophagy and necrotic cell death in multiple myeloma cells. Mol Cancer Ther 2009;8:2441-51.

Nakashima T, Ishii T, Tagaya H, Seike T, Nakagawa H, Kanda Y, et al. New Molecular and Biological Mechanism of Antitumor Activities of KW-2478, a Novel Nonansamycin Heat Shock Protein 90 Inhibitor, in Multiple Myeloma Cells. Clinical Cancer Research 2010;16:2792-802.

Ogawa Y, Tobinai K, Ogura M, Ando K, Tsuchiya T, Kobayashi Y, et al. Phase I and II pharmacokinetic and pharmacodynamic study of the proteasome inhibitor bortezomib in Japanese patients with relapsed or refractory multiple myeloma. Cancer Sci 2008;99:140-4.

Pellat-Deceunynk C, Amiot M, Bataille R, Van Riet I, Van Camp B, Omede P, et al. Human myeloma cell lines as a tool for studying the biology of multiple myeloma: a reappraisal 18 years after. Blood 1995;86:4001-2.

Reece DE, Sullivan D, Lonial S, Mohrbacher AF, Chatta G, Shustik C, et al. Pharmacokinetic and pharmacodynamic study of two doses of bortezomib in patients with relapsed multiple myeloma. Cancer Chemother Pharmacol 2011;67:57-67.

Salmon SE, Hamburger AW, Soehnlen B, Durie BG, Alberts DS, Moon TE. Quantitation of differential sensitivity of human-tumor stem cells to anticancer drugs. N Engl J Med 1978;298:1321-7.

Samuels BL, Bitran JD. High-dose intravenous melphalan: a review. J Clin Oncol 1995;13:1786-99.

San-Miguel JF, Mateos MV. Can multiple myeloma become a curable disease? Haematol-Hematol J 2011;96:1246-8.

Silva AS, Gatenby RA. A theoretical quantitative model for evolution of cancer chemotherapy resistance. Biol Direct 2010;5:25.

Silva AS, Kam Y, Khin ZP, Minton SE, Gillies RJ, Gatenby RA. Evolutionary approaches to prolong progression-free survival in breast cancer. Cancer Res 2012 72:6362-70.

Sternberg SR. Biomedical Image Processing. Computer 1983;16:22-34.

Suggitt M, Bibby MC. 50 years of preclinical anticancer drug screening: Empirical to target-driven approaches. Clinical Cancer Research 2005;11:971-81.

Tang M, Gonen M, Quintas-Cardama A, Cortes J, Kantarjian H, Field C, et al. Dynamics of chronic myeloid leukemia response to long-term targeted therapy reveal treatment effects on leukemic stem cells. Blood 2011;118:1622-31.

Thevenaz P, Ruttimann UE, Unser M. A pyramid approach to subpixel registration based on intensity. IEEE Trans Image Process 1998;7:27-41.

Turner JG, Marchion DC, Dawson JL, Emmons MF, Hazlehurst LA, Washausen P, et al. Human multiple myeloma cells are sensitized to topoisomerase II inhibitors by CRM1 inhibition. Cancer Res 2009;69:6899-905.

Von Hoff DD, Clark GM, Stogdill BJ, Sarosdy MF, O'Brien MT, Casper JT, et al. Prospective clinical trial of a human tumor cloning system. Cancer Res 1983;43:1926-31.

Wells A, Griffith L, Wells JZ, Taylor DP. The Dormancy Dilemma: Quiescence versus Balanced Proliferation. Cancer Res 2013;73:3811-6.

Williamson MJ, Silva MD, Terkelsen J, Robertson R, Yu L, Xia C, et al. The relationship among tumor architecture, pharmacokinetics, pharmacodynamics, and efficacy of bortezomib in mouse xenograft models. Mol Cancer Ther 2009;8:3234-43.

Yanamandra N, Colaco NM, Parquet NA, Buzzeo RW, Boulware D, Wright G, et al. Tipifarnib and bortezomib are synergistic and overcome cell adhesion-mediated drug resistance in multiple myeloma and acute myeloid leukemia. Clin Cancer Res 2006;12:591-9.

\* cited by examiner

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| A | | | | | | | | | | | | | | | | | | | | | | | | |
| B | | MEL | CF2 | DEX | ADR | KPT | PAN | QST | MEL | DEX | DEX | POM | POM | REV | REV | | MEL | DEX | DEX | DEX | POM | POM | REV | REV |
| C | | 1 | 2 | 3 | 4 | 5 | 6 | 7 | 8 | 9 | 10 | 11 | 12 | 13 | 14 | | 15 | 16 | 17 | 18 | 19 | 20 | 21 | |
| D | | 42 | 41 | 40 | 39 | 38 | 37 | 36 | 35 | 34 | 33 | 32 | 31 | 30 | 29 | | 28 | 27 | 26 | 25 | 24 | 23 | 22 | |
| E | | 43 | 44 | 45 | 46 | 47 | 48 | 49 | 50 | 51 | 52 | 53 | 54 | 55 | 56 | | 57 | 58 | 59 | 60 | 61 | 62 | 63 | |
| F | | 84 | 83 | 82 | 81 | 80 | 79 | 78 | 77 | 76 | 75 | 74 | 73 | 72 | 71 | | 70 | 69 | 68 | 67 | 66 | 65 | 64 | |
| G | | 85 | 86 | 87 | 88 | 89 | 90 | 91 | 92 | 93 | 94 | 95 | 96 | 97 | 98 | | 99 | 100 | 101 | 102 | 103 | 104 | 105 | |
| H | | | | | 114 | | | | | 112 | 111 | 110 | | | | | 109 | 108 | 107 | 106 | | | | |
| I | | 117 | 116 | 115 | | | | | 113 | | | | | | | | | | | | | | | |
| J | | 118 | 119 | 120 | 121 | 122 | 123 | 124 | 125 | 126 | 127 | 128 | 129 | 130 | 131 | | 132 | 133 | 134 | 135 | 136 | 137 | 138 | |
| K | | 159 | 158 | 157 | 156 | 155 | 154 | 153 | 152 | 151 | 150 | 149 | 148 | 147 | 146 | | 145 | 144 | 143 | 142 | 141 | 140 | 139 | |
| L | | 160 | 161 | 162 | 163 | 164 | 165 | 166 | 167 | 168 | 169 | 170 | 171 | 172 | 173 | | 174 | 175 | 176 | 177 | 178 | 179 | 180 | |
| M | | 201 | 200 | 199 | 198 | 197 | 196 | 195 | 194 | 193 | 192 | 191 | 190 | 189 | 188 | | 187 | 186 | 185 | 184 | 183 | 182 | 181 | |
| N | | 202 | 203 | 204 | 205 | 206 | 207 | 208 | 209 | 210 | 211 | 212 | 213 | 214 | 215 | | 216 | 217 | 218 | 219 | 220 | 221 | 222 | |
| O | | 50uM | 50nM | 50uM | 5uM | 3uM | 30nM | 30nM | 50uM | 100uM | 100uM | 100uM | 100uM | 100uM | 100uM | | 50uM | 100uM | 100uM | 100uM | 100uM | 100uM | 100uM | |
| P | | | | | | | | | | | | | | | | | | | | | | | | |

FIG. 16

| PATIENT | TIME (MONTHS) | CLINICAL BURDEN (% ORIGINAL) | EX VIVO BURDEN (%ORIGINAL) | | | TREATMENT | DRUG EX VIVO |
|---|---|---|---|---|---|---|---|
| | | | MEAN | MIN | MAX | | |
| Pt6 | 0.7 | 285.7 | 135.3 | 115.0 | 155.6 | NPI-0052 | V |
| Pt7 | 0.9 | 250 | 150.5 | 121.0 | 180.0 | CFZ+CD | V |
| Pt7 | 1.9 | 250 | 236.5 | 148.0 | 325.0 | CFZ+CD | V |
| Pt7 | 2.1 | 250 | 266.5 | 156.0 | 377.0 | CFZ+CD | V |
| Pt9 | 0.8 | 108 | 104.5 | 100.0 | 109.0 | NPI-0052 | V |
| Pt9 | 1.8 | 108 | 110.0 | 100.0 | 120.0 | NPI-0052 | V |
| Pt9 | 2.5 | 129 | 115.0 | 100.0 | 130.0 | NPI-0052 | V |
| Pt9 | 2.6 | 150.0 | 115.5 | 100.0 | 131.0 | NPI-0052 | V |
| Pt10 | 1.0 | 103.0 | 130.6 | 122.6 | 138.5 | CFZ+THAL+DEX | V |
| Pt11 | 0.6 | 65.1 | 68.5 | 68.0 | 69.0 | VD | V |
| Pt11 | 0.8 | 52.5 | 55.0 | 54.0 | 56.0 | VD | V |
| Pt11 | 2.2 | 27.5 | 26.5 | 23.0 | 30.0 | VD | V |
| Pt12 | 0.8 | 0.0 | 39.6 | 39.1 | 40.0 | VRD | V |
| Pt14 | 0.7 | 48.4 | 57.9 | 56.0 | 59.8 | VD | V |
| Pt14 | 1.4 | 29.0 | 21.7 | 20.7 | 22.7 | VD | V |
| Pt15 | 1.6 | 20 | 24.9 | 23.3 | 26.5 | VRD | V |
| Pt18 | 0.2 | 117 | 86.4 | 85.8 | 86.9 | OPR+D | V |
| Pt18 | 1.2 | 66.7 | 21.1 | 20.9 | 21.2 | OPR+D | V |
| Pt18 | 2.1 | 38.9 | 5.5 | 5.5 | 5.6 | OPR+D | V |
| Pt21 | 3.2 | 155.6 | 108.0 | 63.0 | 153.0 | V(MAINT.) | V |

FIG. 29

METHODS FOR ASSESSING CELL VIABILITY OR PREDICTING CELL RESPONSE TO A TREATMENT USING CELL MOVEMENT

CROSS-REFERENCE TO RELATED APPLICATIONS

This application claims benefit of priority to U.S. Provisional Application No. 61/904,550, filed Nov. 15, 2013, which is hereby incorporated herein by reference in its entirety.

STATEMENT REGARDING FEDERALLY SPONSORED RESEARCH OR DEVELOPMENT

This invention was made with Government Support under Grant No. CA143803 and Grant No. CA164322 awarded by the National Institutes of Health. The Government has certain rights in the invention.

BACKGROUND

The purposes of pre-clinical systems range from early identification of compounds with anti-cancer activity, estimation of patient-specific clinical response, or the discovery of novel targetable cellular mechanisms (Suggitt M, Bibby M C. Clinical Cancer Research 2005; 11:971-81; Von Hoff D D, Clark G M, et al. Cancer Res 1983; 43:1926-31). All available systems have strengths and limitations: in vitro assays using cell lines are scalable, reproducible and inexpensive, but cell lines are significantly different from their originating tumors (Pellat-Deceunynk C, Amiot M, et al. Blood 1995; 86:4001-2), and the tumor microenvironment's effects are often absent in these assays. Animal models include more realistic elements such as drug pharmacokinetics and influence of the tumor microenvironment, but they often rely on cell lines, require long-term experiments, and carry significant financial cost. Irrespective of the pre-clinical model used, the data generated cannot be directly ported into clinical estimations without the help of an adequate computational framework.

Computational modeling has long been used to study the dynamics of tumor response to therapy, as well as emergence of drug resistance (Hokanson J A, Brown B W, et al. Cancer 1977; 39:1077-84; Chmielecki J, Foo J, et al. Sci Transl Med 2011; 3:90ra59; Tang M, Gonen M, et al. Blood 2011; 118:1622-31). These theoretical models are powerful tools for analyzing complex interactions like the tumor-host-therapy system, and could, in a near future, become decision-support systems for oncologists, making personalized oncology a possibility (Gardner S N, Fernandes M. Mol Cancer Ther 2003; 2:1079-84). The Achilles' heel of such models, however, is the reliability of the experimental data used to parameterize them. More often than not, these computational models are parameterized by data from literature, in many cases from experiments that have been performed at incompatible conditions.

Four decades ago, Salmon and collaborators (Salmon S E, Hamburger A W, et al. N Engl J Med 1978; 298:1321-7) proposed an in vitro method for estimation of clinical response of cancer patients based on the capacity of primary cancer cells to form colonies at physiologically reachable chemotherapy concentrations. The main limitation of these early assays, however, was the small number of patient samples that were capable of forming colonies under control conditions. With a cloning efficiency between 0.001% and 0.1%, the growth of colonies in vitro was a challenge comparable to surviving the chemotherapeutic insult itself. Consequently, these restrictions limited the number of drugs, concentrations and time points that could be studied for a single patient (Suggitt M, Bibby M C. Clin Cancer Res 2005; 11:971-81), even in more recent models (Kirshner J, Thulien K J, et al. Blood 2008; 112:2935-4). Finally, the outcome of these assays were often dichotomized, in other words, either a patient was "sensitive" or "resistant" to the drug, but no information was provided regarding duration of response and time to relapse. Given that in many cancers the overall survival is more dependent on the duration of the response than on its depth (Durie B G, Jacobson J, et al. J Clin Oncol 2004; 22:1857-63; Harousseau J L, Attal M, Avet-Loiseau H. Blood 2009; 114:3139-46), the application of these early assays as predictive biomarkers was somewhat limited.

The methods disclosed herein address these and other limitations.

SUMMARY

Disclosed herein are non-destructive methods for quantifying cell viability. In some examples, the method can comprise culturing a plurality of cells from a subject in a chamber; capturing a first optical signal from the cells at a first time point; capturing a second optical signal from the cells at a second time point; analyzing the first optical signal and the second optical signal to detect cell membrane motion of the cells; and analyzing the cell membrane motion to quantify the viability of the cells. In some embodiments, the method is used to quantify cell viability after the cells have been contacted with an active agent.

Any cell type can be assayed by the disclosed methods. For example, the methods can be used to test for toxicity of a candidate agent on normal cells. Alternatively, the methods can be used to test cytotoxicity of a drug on abnormal cells, such as an antineoplastic drug on cancer cells. Therefore, in some examples, the cells are cancer cells, which can include solid tumor cells or hematological cancer cells (e.g., multiple myeloma).

The chamber of the disclosed method can be any chamber suitable to culture cells and allow imaging of the cells while in culture. For example, in some examples, the chamber is a microfluidic chamber. In some examples, the chamber is a well in a multiwell-plate.

In some examples, the chamber can recapitulate the cell's natural microenvironment. This can involve the use of growth media, polymer substrates, feeder cells, stromal cells, growth factors, and the like. In some cases, the chamber recapitulates a cancer microenvironment. For example, culturing hematological cancer cells can involve a 3D reconstruction of the cancer microenvironment, e.g., including primary hematological cancer cells, extracellular matrix, patient-derived stroma, and growth factors.

In some examples, the active agent can comprise an anticancer agent, such as a chemotherapeutic agent. In some examples, the active agent can comprise a combination of active agents. For example, the anticancer agent can be a composition comprising melphalan, bortezomib, FAM-HYD-1, Marizomib (NPI-0052), Carfilzomib, Cytoxan, Dexamethasone, Thalidomide, Lenalidomide, Oprozomib, Panobinostat, Quisinostat, and Selinexor, or any combination thereof.

In some examples, the first optical signal, the second optical signal, or a combination thereof involves any optical microscopy illumination techniques suitable to detect cell membrane activity, such as a bright field illumination, dark field illumination, and phase contrast illumination.

In some examples, the cells of the method are obtained by collecting a sample from the subject and then isolating the cells from the sample. As an example, the sample can comprise a bone marrow aspirate where the cells are hematological cancer cells isolated from the aspirate, e.g., by flow cytometry using a cell surface cancer marker.

In some examples, the method can further comprise collecting parameters from the viability observations to generate a multi-parameter model that summarizes the response of a cancer in a subject to the active agent.

Also disclosed herein are methods for predicting a response of a subject to treatment with an active agent. The methods can comprise first preparing a three-dimensional dose-response curve by assessing the viability of cells from the subject in response to the active agent at a plurality of time points at a plurality of dosages. The method can then involve generating a multi-parameter model that summarizes the three-dimensional dose-response curve. The multi-parameter model can then be used to calculate the rate of accumulation of damage in the cells due to the active agent and the active agent-induced cell death due to the accumulated damage. In some embodiments, the number of distinct populations in the cells is a covariate in the multi-parameter model, so the method can involve determining the number of populations. The rate of accumulation of damage in the cells and the active agent-induced cell death due to the accumulated damage can then be extrapolated to predict a response of the subject to the active agent. For example, a three-dimensional dose-response curve based on 2, 3, 4, 5, 6, 7 days of viability data can be extrapolated to 1, 2, 3, 4, 5, 6, 7, 8, 9, 10, or more years of response by the subject.

In some examples, the methods disclosed herein can further comprise selecting a cancer treatment regimen for the subject based on predicted responses to 2, 3, 4, 5, 6, 7, 8, 9, 10, or more different active agents.

In some examples, the method can predict an initial response of the subject to the active agent. In some examples, the method can predict the chance of progression-free survival. In some examples, the method can predict the chance of developing environment-mediated resistance to the active agent. In some examples, the method can predict an effective dosing schedule of the active agent. In some examples, the method can predict an effective concentration of the active agent.

Also disclosed herein are platforms to study drug response in cancer. In particular, methods for selecting a cancer treatment regimen for a subject are disclosed. The method can first involve administering cancer cells from the subject to a chamber that recapitulates the cancer microenvironment. For example, the chamber can contain 3D extracellular matrix and mesenchymal cells derived from the tumor microenvironment. The chamber can further contain the drug to be tested present in a linear gradient across the chamber. The method can then involve detecting cell death induced by the drug across the drug gradient at one or more time points. These and other parameters collected from the assay can then be used to generate a multi-parameter model that summarizes the response of the subject to the drug treatment. This is preferably done using computational modeling. The method can be used to select a cancer treatment regimen for the subject based on the results of the multi-parameter model.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2 depicts four examples of these cells exposed to 50 μM melphalan for 24 h. The first column depicts the initial time point, when all cells are alive. The red fluorescent channel was superimposed to the transmitted light, while the motion detection algorithm pseudo-colored them as green. The second column shows the moment of loss of membrane motion, while the third column shows the moment of loss of red fluorescence. The last column represents the last time point, when Calcein AM was added to identify live cells.

FIG. 3 shows four examples of H929/S cells exposed to a stable drug gradient of Melphalan, from 50 to 10 μM. At the beginning of the experiment, all live cells were pseudo-colored in green from motion detection. The moment of loss of membrane motion was marked by the disappearance of green in the image. There was a variable delay between loss of membrane motion and acquisition of red fluorescence, which is a combination of loss of membrane integrity and binding of EthD-1 to DNA.

FIG. 16: Schematic of an example multiwell plate. In this example, one sample from a patient (wells in columns 2-8 and rows B-L) was tested for sensitivity to 7 drugs: melphalan (MEL), carfilzomib (CFZ), dexamethasone (DEX), doxorubicin (a.k.a. Adriamycin, ADR), Selinexor (KPT), Panobinostat (PAN) and Quisinostat (QST). The highest concentrations of drug were on row 'B' and are serially diluted 3-fold every row from 'C' to 'F', thus 5 different drug concentrations for each drug. The same pattern was repeated from line 'H' until 'L', representing the second replicate. Squares 114-117 represent the controls: the cells in these wells did not receive any drug. The concentrations in row 'M' are the highest concentration for each drug in the panel. In the same plate, a second experiment was performed to assess how the microenvironment can affect drug efficacy. For this experiment, a multiple myeloma cell line in co-culture with mesenchymal stem cells in collagen matrix (columns 10-16, rows B-E and columns 11 and 12 on row G), in single culture in collagen matrix (columns 12, 13, 20, and 21 on row G, and columns 10-16 and 18-24 on rows H-L) and in single culture in media (Columns 18-24, rows B-F, and columns 18 and 19 on row G) were used.

FIG. 29: Actual and estimated normalized tumor burden for multiple myeloma patients treated in proteasome inhibitor-based regimens. 10 multiple myeloma patients who donated bone marrow aspirates for the assay described herein were followed after treatment. Each entry in the column 'Time (months)' represents the delay (in months) between the tumor burden measurement and the original biopsy. Column 'Clinical Burden (% original)' represents the tumor burden measurement at that particular moment in time normalized by the tumor burden at the time of biopsy. 'Mean' is the average between the model estimations for best ('Min') and worst ('Max') case scenarios, which correspond to smallest and largest tumor estimation. 'Treatment' represents the actual clinical treatment received by the patient. 'Drug Ex vivo' represents the drug used to test the sensitivity of the cells of these patients and create the estimations of clinical response.

DETAILED DESCRIPTION

Figure 1:
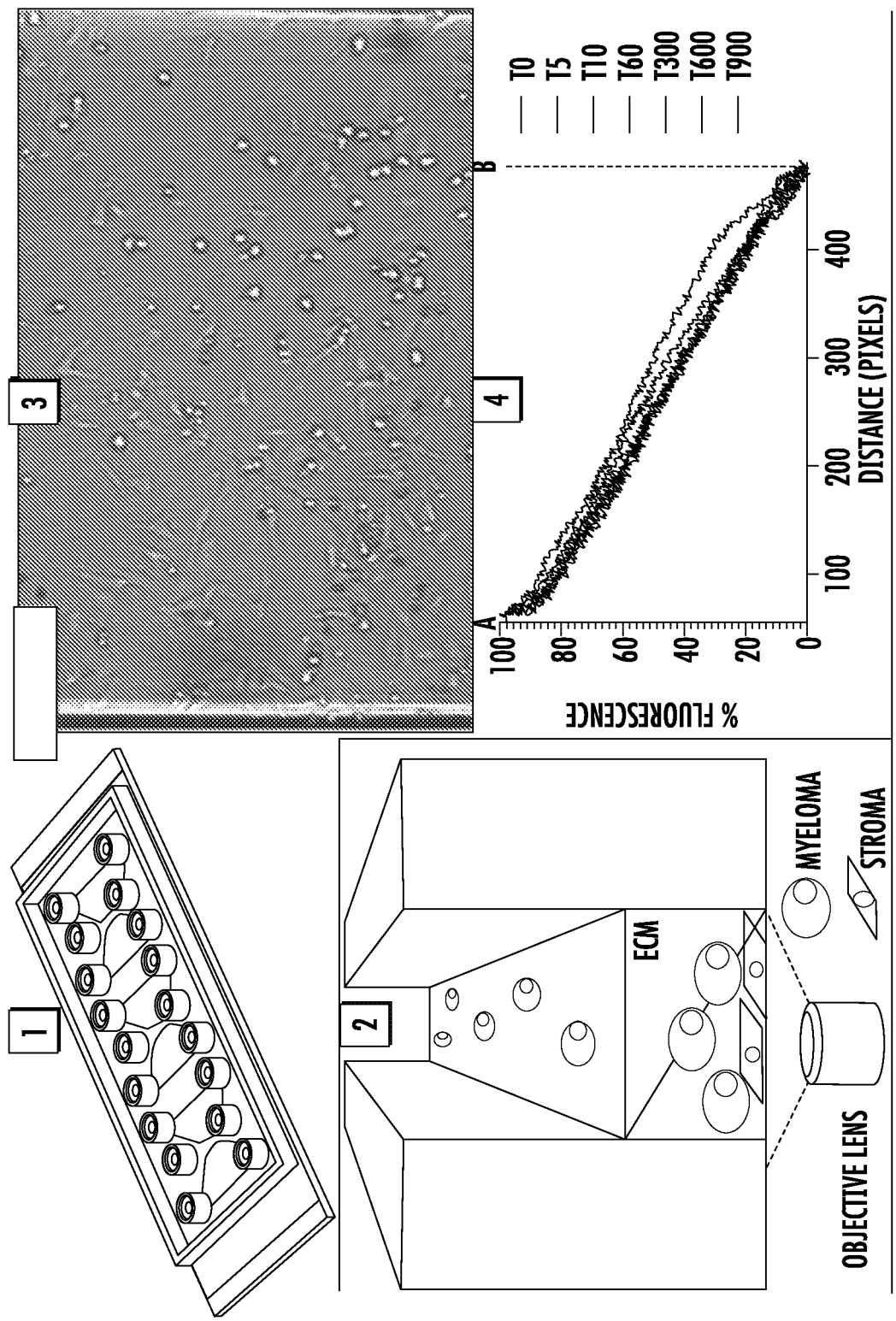
FIG. 1: Schematic view of microfluidic assay used for in vitro reconstruction of bone marrow. (1) Each microfluidic chip contained three chambers, each of them composed of two side reservoirs, and one center observation chamber. Myeloma and stromal cells were loaded in the observation chamber simultaneously, resuspended in collagen. Overnight, the matrix gellifies, and stromal cells adhered to the bottom of the chamber and stretch. (2) One of the side reservoirs was filled with medium with a chemotherapeutic agent (left), while the other was filled with standard growth medium (right). The diffusion of the chemotherapeutic agent from one reservoir to the other created a stable gradient across the observation chamber. (3) The observation channel with the human MM cell line NCI-H929 and adherent bone marrow derived stromal cell line HS-5 is shown in bright field under a gradient of the necrosis-inducing peptide HYD-1. Note that MM cells on the left (higher drug concentration) have died and became dark spots, while cells on the right (lower drug concentration) are still alive. (4) A gradient of the fluorescent conjugated peptide FAM-HYD1 was established, and fluorescence quantified across the channel during 18 h. Normalization and re-scaling to the minimum and maximum concentration within the observation channel confirm the linear stable gradient during the 18 h window of experiment.

The methods described herein may be understood more readily by reference to the following detailed description of specific aspects of the disclosed subject matter and the Examples and Figures included therein.

Before the present methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an agent" includes mixtures of two or more such agents, reference to "the component" includes mixtures of two or more such components, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. By "about" is meant within 5% of the value, e.g., within 4, 3, 2, or 1% of the value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

The term "inhibit" refers to a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The term "subject" refers to any individual who is the target of administration or treatment. The subject can be a vertebrate, for example, a mammal Thus, the subject can be a human or veterinary patient. The term "patient" refers to a subject under the treatment of a clinician, e.g., physician.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

The term "treat," or other forms of the word, such as "treated" or "treatment," refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "anticancer" refers to the ability to treat or control cellular proliferation and/or tumor growth at any concentration.

The term "cell membrane motion" refers to any detectable movement of or within a cell's membrane that ceases once the cell is dead.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Reference will now be made in detail to specific aspects of the disclosed materials, compounds, compositions, articles, and methods, examples of which are illustrated in the accompanying Examples and Figures.

Methods

Accurate preclinical predictions of the clinical efficacy of experimental cancer drugs are highly desired but often haphazard. Such predictions can be improved by incorporating elements of the tumor microenvironment in preclinical models by providing a more physiological setting. In generating improved xenograft models, the use of primary tumors from patients is preferable to clonal tumor cell lines.

Disclosed herein are systems and methods comprising a dose-response platform, for in vitro screening of drugs. Also disclosed herein are systems and methods comprising a computational model of clinical response. In some examples, the systems and methods can combine the dose-response platform, for in vitro screening of drugs and the computational model of clinical response. In some examples, the in vitro component can include a 3D reconstruction of a cancer microenvironment, e.g., including primary cancer cells, extracellular matrix, and patient-derived stroma and growth factors. In some examples, live microscopy and digital image analysis can be used to detect cell death events in different drug concentrations, which can then be used to generate dose-response surfaces. In some examples, an evolutionary computational model designed to simulate how a heterogeneous population of cancer cells responds to therapy is used as an in silico component of the methods described herein. From the in vitro data, the model can identify the size and chemosensitivity of subpopulations within the patient's tumor burden, and simulate how the tumor would respond to the drug(s) in physiological conditions in a clinical regimen.

Pre-clinical assays specifically designed to generate data to parameterize such computational models, preferably comply with one or more of the following conditions: (a) compatibility with patient primary cancer cells; (b) recapitulate the tumor microenvironment, namely extra-cellular matrix and stroma; (c) be non-destructive, so longitudinal studies can be performed, incorporating the temporal dimension; (d) use as few cells per experimental condition as possible, so each patient sample could be tested against a panel of chemotherapeutic agents, in different environmental conditions; and (e) the data generated should result in testable clinical predictions, such as the depth of response and/or progression-free survival (PFS).

Disclosed herein are non-destructive methods for quantifying cell viability. In some examples, the method can comprise culturing a plurality of cells from a subject in a chamber; capturing a first optical signal from the cells at a first time point; capturing a second optical signal from the cells at a second time point; analyzing the first optical signal and the second optical signal to detect cell membrane motion of the cells; and analyzing the cell membrane motion to quantify the viability of the cells. In some embodiments, the method is used to quantify cell viability after the cells have been exposed to an active agent. Therefore, in some embodiments, the method further comprises contacting the cells with an active agent and then quantifying the effect of the active agent on cell membrane motion (i.e., viability).

In some examples, the cells can comprise cancer. Examples include cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Other examples of cancers include adrenocortical carcinoma, adrenocortical carcinoma, cerebellar astrocytoma, basal cell carcinoma, bile duct cancer, bladder cancer, bone cancer, brain tumor, breast cancer, Burkitt's lymphoma, carcinoid tumor, central nervous system lymphoma, cervical cancer, chronic myeloproliferative disorders, colon cancer, cutaneous T-cell lymphoma, endometrial cancer, ependymoma, esophageal cancer, gallbladder cancer, gastric (stomach) cancer, gastrointestinal carcinoid tumor, germ cell tumor, glioma, hairy cell leukemia, head and neck cancer, hepatocellular (liver) cancer, hypopharyngeal cancer, hypothalamic and visual pathway glioma, intraocular melanoma, retinoblastoma, islet cell carcinoma (endocrine pancreas), laryngeal cancer, lip and oral cavity cancer, liver cancer, medulloblastoma, Merkel cell carcinoma, squamous neck cancer with occult mycosis fungoides, myelodysplastic syndromes, myelogenous leukemia, nasal cavity and paranasal sinus cancer, nasopharyngeal cancer, neuroblastoma, non-small cell lung cancer, oral cancer, oropharyngeal cancer, osteosarcoma, ovarian cancer, pancreatic cancer, paranasal sinus and nasal cavity cancer, parathyroid cancer, penile cancer, pheochromocytoma, pineoblastoma and supratentorial primitive neuroectodermal tumor, pituitary tumor, plasma cell neoplasm/multiple myeloma, pleuropulmonary blastoma, prostate cancer, rectal cancer, renal cell (kidney) cancer, retinoblastoma, rhabdomyosarcoma, salivary gland cancer, Ewing's sarcoma, soft tissue sarcoma, Sezary syndrome, skin cancer, small cell lung cancer, small intestine cancer, supratentorial primitive neuroectodermal tumors, testicular cancer, thymic carcinoma, thymoma, thyroid cancer, transitional cell cancer of the renal pelvis and ureter, trophoblastic tumor, urethral cancer, uterine cancer, vaginal cancer, vulvar cancer, Waldenström's macroglobulinemia, and Wilms' tumor.

In some examples, the cancer can comprise a hematological cancer. Hematological cancers are the types of cancer that affect blood, bone marrow and lymph nodes. As the three are intimately connected through the immune system, a disease affecting one of the three will often affect the others as well. Hematological cancers may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid cell line, while acute and chronic myelogenous leukemia, myelodysplastic syndromes and myeloproliferative diseases are myeloid in origin.

In some examples, the cancer can comprise multiple myeloma. Multiple myeloma is the second most common hematological cancer in the United States, and constitutes 1% of all cancers. Specifically, multiple myeloma is a cancer of plasma cells, a type of white blood cell normally responsible for producing antibodies. In multiple myeloma, collections of abnormal plasma cells accumulate in the bone marrow, where they interfere with the production of normal blood cells. Kidney problems, bone lesions and hypercalcemia are common complications associated with multiple myeloma. Myeloma develops in 1-4 per 100,000 people per year. It is more common in men, and is twice as common in African-Americans as it is in European-Americans. With conventional treatment, median survival is 3-4 years, which may be extended to 5-7 years or longer with advanced treatments.

The chamber can comprise any chamber consistent with the methods described herein. Examples of suitable chambers can include, but are not limited to, petri dishes, laboratory flasks (e.g., Erlenmeyer flasks, beakers, conical flasks, round bottom flasks, culture flasks), microfluidic chambers, multiwell-pates, and the like. In some examples, the chamber can comprise any chamber that allows for bright field imaging. In some examples, the chamber can comprise a microfluidic chamber. In some examples, the chamber can comprise a well in a multiwell-plate.

In some examples, the chamber can recapitulate the cancer microenvironment. In some examples, the culturing a plurality of cancer cells from a subject in a chamber can include a 3D reconstruction of the cancer microenvironment, e.g., including primary cancer cells, extracellular matrix, and patient-derived stroma and growth factors.

The active agent can comprise a wide variety of drugs, including antagonists, for example enzyme inhibitors, and agonists, for example a transcription factor which results in an increase in the expression of a desirable gene product (although as will be appreciated by those in the art, antagonistic transcription factors can also be used), are all included. In addition, the active agent includes those agents capable of direct toxicity and/or capable of inducing toxicity towards healthy and/or unhealthy cells in the body. Also, the active agent can be capable of inducing and/or priming the immune system against potential pathogens.

The active agent can, for example, comprise an anticancer agent, antiviral agent, antimicrobial agent, anti-inflammatory agent, immunosuppressive agent, anesthetics, or any combination thereof.

In some examples, the active agent can comprise an anticancer agent. Examples of anticancer agents include 13-cis-Retinoic Acid, 2-Amino-6-Mercaptopurine, 2-CdA, 2-Chlorodeoxyadenosine, 5-fluorouracil, 6-Thioguanine, 6-Mercaptopurine, Accutane, Actinomycin-D, Adriamycin, Adrucil, Agrylin, Ala-Cort, Aldesleukin, Alemtuzumab, Alitretinoin, Alkaban-AQ, Alkeran, All-transretinoic acid, Alpha interferon, Altretamine, Amethopterin, Amifostine, Aminoglutethimide, Anagrelide, Anandron, Anastrozole, Arabinosylcytosine, Aranesp, Aredia, Arimidex, Aromasin, Arsenic trioxide, Asparaginase, ATRA, Avastin, BCG, BCNU, Bevacizumab, Bexarotene, Bicalutamide, BiCNU, Blenoxane, Bleomycin, Bortezomib, Busulfan, Busulfex, C225, Calcium Leucovorin, Campath, Camptosar, Camptothecin-11, Capecitabine, Carac, Carboplatin, Carmustine, Carmustine wafer, Casodex, CCNU, CDDP, CeeNU, Cerubidine, cetuximab, Chlorambucil, Cisplatin, Citrovorum Factor, Cladribine, Cortisone, Cosmegen, CPT-11, Cyclophosphamide, Cytadren, Cytarabine, Cytarabine liposomal, Cytosar-U, Cytoxan, Dacarbazine, Dactinomycin, Darbepoetin alfa, Daunomycin, Daunorubicin, Daunorubicin hydrochloride, Daunorubicin liposomal, DaunoXome, Decadron, Delta-Cortef, Deltasone, Denileukin diftitox, DepoCyt, Dexamethasone, Dexamethasone acetate, Dexamethasone sodium phosphate, Dexasone, Dexrazoxane, DHAD, DIC, Diodex, Docetaxel, Doxil, Doxorubicin, Doxorubicin liposomal, Droxia, DTIC, DTIC-Dome, Duralone, Efudex, Eligard, Ellence, Eloxatin, Elspar, Emcyt, Epirubicin, Epoetin alfa, Erbitux, Erwinia L-asparaginase, Estramustine, Ethyol, Etopophos, Etoposide, Etoposide phosphate, Eulexin, Evista, Exemestane, Fareston, Faslodex, Femara, Filgrastim, Floxuridine, Fludara, Fludarabine, Fluoroplex, Fluorouracil, Fluorouracil (cream), Fluoxymesterone, Flutamide, Folinic Acid, FUDR, Fulvestrant, G-CSF, Gefitinib, Gemcitabine, Gemtuzumab ozogamicin, Gemzar, Gleevec, Lupron, Lupron Depot, Matulane, Maxidex, Mechlorethamine, -Mechlorethamine Hydrochlorine, Medralone, Medrol, Megace, Megestrol, Megestrol Acetate, Melphalan, Mercaptopurine, Mesna, Mesnex, Methotrexate, Methotrexate Sodium, Methylprednisolone, Mylocel, Letrozole, Neosar, Neulasta, Neumega, Neupogen, Nilandron, Nilutamide, Nitrogen Mustard, Novaldex, Novantrone, Octreotide, Octreotide acetate, Oncospar, Oncovin, Ontak, Onxal, Oprevelkin, Oraprep, Orasone, Oxaliplatin, Paclitaxel, Pamidronate, Panretin, Paraplatin, Pediapred, PEG Interferon, Pegaspargase, Pegfilgrastim, PEG-INTRON, PEG-L-asparaginase, Phenylalanine Mustard, Platinol, Platinol-AQ, Prednisolone, Prednisone, Prelone, Procarbazine, PROCRIT, Proleukin, Prolifeprospan 20 with Carmustine implant, Purinethol, Raloxifene, Rheumatrex, Rituxan, Rituximab, Roveron-A (interferon alfa-2a), Rubex, Rubidomycin hydrochloride, Sandostatin, Sandostatin LAR, Sargramostim, Solu-Cortef, Solu-Medrol, STI-571, Streptozocin, Tamoxifen, Targretin, Taxol, Taxotere, Temodar, Temozolomide, Teniposide, TESPA, Thalidomide, Thalomid, TheraCys, Thioguanine, Thioguanine Tabloid, Thiophosphoamide, Thioplex, Thiotepa, TICE, Toposar, Topotecan, Toremifene, Trastuzumab, Tretinoin, Trexall, Trisenox, TSPA, VCR, Velban, Velcade, VePesid, Vesanoid, Viadur, Vinblastine, Vinblastine Sulfate, Vincasar Pfs, Vincristine, Vinorelbine, Vinorelbine tartrate, VLB, VP-16, Vumon, Xeloda, Zanosar, Zevalin, Zinecard, Zoladex, Zoledronic acid, Zometa, Gliadel wafer, Glivec, GM-CSF, Goserelin, granulocyte colony stimulating factor, Halotestin, Herceptin, Hexadrol, Hexalen, Hexamethylmelamine, HMM, Hycamtin, Hydrea, Hydrocort Acetate, Hydrocortisone, Hydrocortisone sodium phosphate, Hydrocortisone sodium succinate, Hydrocortone phosphate, Hydroxyurea, Ibritumomab, Ibritumomab Tiuxetan, Idamycin, Idarubicin, Ifex, IFN-alpha, Ifosfamide, IL 2, IL-11, Imatinib mesylate, Imidazole Carboxamide, Interferon alfa, Interferon Alfa-2b (PEG conjugate), Interleukin 2, Interleukin-11, Intron A (interferon alfa-2b), Leucovorin, Leukeran, Leukine, Leuprolide, Leurocristine, Leustatin, Liposomal Ara-C, Liquid Pred, Lomustine, L-PAM, L-Sarcolysin, Meticorten, Mitomycin, Mitomycin-C, Mitoxantrone, M-Prednisol, MTC, MTX, Mustargen, Mustine, Mutamycin, Myleran, Iressa, Irinotecan, Isotretinoin, Kidrolase, Lanacort, L-asparaginase, LCR, FAM-HYD-1, Marizomib (NPI-0052), Lenalidomide, Carfilzomib, Panobinostat, Quisinostat, Selinexor, and Oprozomib. The anticancer agent can also include biopharmaceuticals such as, for example, antibodies.

In some examples, the active agent can comprise a combination of active agents.

In some examples, the active agent can comprise melphalan, bortezomib, FAM-HYD-1, Marizomib (NPI-0052), Carfilzomib, Cytoxan, Dexamethasone, Thalidomide, Lenalidomide, Oprozomib, Panobinostat, Quisinostat, Selinexor, or a combination thereof. Bortezomib, carfilzomib, and oprozomib are proteasome inhibitors, whereas melphalan is an alkylating agent. They are approved for the treatment of multiple myeloma, as well as other diseases. FAM-HYD-1 is a conjugate of the fluorescent molecule fluorescein (FAM) and the 1.5 kDa peptide HYD-1, an experimental drug with direct toxicity to MM cells (Nair R R, Emmons M F, et al. Mol Cancer Ther 2009; 8:2441-51). Panobinostat and Quisinostat are experimental histone deacetylase (HDAC) inhibitors in clinical trials for treatment of multiple myeloma patients. Selinexor is a nuclear export inhibitor also in clinical trials for treatment of multiple myeloma.

Contacting the cells with the active agent can be accomplished by any suitable method and technique presently or prospectively known to those skilled in the art. Administration of the active agent can be a single administration, or at continuous or distinct intervals as can be readily determined by a person skilled in the art.

In some examples, the first optical signal, the second optical signal, or a combination thereof involves any optical microscopy illumination techniques suitable to detect cell membrane activity, such as a bright field illumination, dark field illumination, and phase contrast illumination.

Cell membrane motion can comprise, for example, observable changes in the size and/or morphology of the cell membrane (e.g., cell membrane motion does not comprise translational motion of the cell). In some examples, the absence of cell membrane motion can indicate cell death.

In some examples, the cells of the method are obtained by collecting a sample from the subject and then isolating the cells from the sample. As an example, the sample can comprise a bone marrow aspirate where the cells are hematological cancer cells isolated from the aspirate, e.g., by flow cytometry using a cell surface cancer marker.

In some examples, the method can further comprise collecting parameters from the viability observations to generate a multi-parameter model that summarizes the response of a cancer in a subject to the active agent. These parameters can include, for example, drug concentration, exposure time, IC50, EC50, and drug free doubling time, as well as clinical information from the patient, such as previous response to drugs and rate of tumor regrowth as measured by surrogate measurements such as blood or urine para-proteins. Computational methods, such as those disclosed herein, may be parameterized by data from the disclosed method and used to estimate response to treatment with the drug being tested.

Also disclosed herein are methods for predicting a response of a subject to treatment with an active agent. The methods can comprise first preparing a three-dimensional dose-response curve by assessing the viability of cells from the subject in response to the active agent at a plurality of time points at a plurality of dosages. The method can then involve generating a multi-parameter model that summarizes the three-dimensional dose-response curve. The multi-parameter model can then be used to calculate the rate of accumulation of damage in the cells due to the active agent and the active agent-induced cell death due to the accumulated damage. In some embodiments, the number of distinct populations (e.g., in terms of sensitivity to the active agent) in the cells is a covariate in the multi-parameter model, so the method can involve determining the number of populations. The rate of accumulation of damage in the cells and the active agent-induced cell death due to the accumulated damage can then be extrapolated to predict a response of the subject to the active agent. For example, a three-dimensional dose-response curve based on 2, 3, 4, 5, 6, 7 days of viability data can be extrapolated to 1, 2, 3, 4, 5, 6, 7, 8, 9, 10, or more years of response by the subject.

In some examples, assessing the viability of the plurality of cells can comprise any of the methods described above.

In some examples, the methods disclosed herein can further comprise selecting a cancer treatment regimen for the subject based on predicted responses to 2, 3, 4, 5, 6, 7, 8, 9, 10, or more different active agents.

In some examples, the method can predict an initial response of the subject to the active agent. In some examples, the method can predict the chance of progression-free survival. In some examples, the method can predict the chance of developing environment-mediated resistance to the active agent. In some examples, the method can predict an effective dosing schedule of the active agent. In some examples, the method can predict an effective concentration of the active agent.

The methods disclosed herein can be carried out in whole or in part on one or more computing device. Therefore, also disclosed is a computer system comprising memory on which is stored instructions to perform the disclosed methods. Also disclosed herein are devices and modules within a device, wherein the device or module is configured to perform the disclosed methods. For example, the memory can contain instructions to receive optical signals from a device (e.g., imager), analyze the first optical signal and the second optical signal to detect cell membrane motion of the cells, and analyze the cell membrane motion to quantify the viability of the cells following contact with the active agent. In some examples, the memory can contain instructions to utilize a dose-response curve to develop a multi-parameter model, wherein the multi-parameter model describes the rate of accumulation of damage in the cells due to the active agent and the active agent-induced cell death due to the accumulated damage; utilize the multi-parameter model and the dose-response curve to determine the number of populations in the sample; and utilize the number of populations and the multi-parameter model to predict a response of the subject to the active agent.

Figure 30:
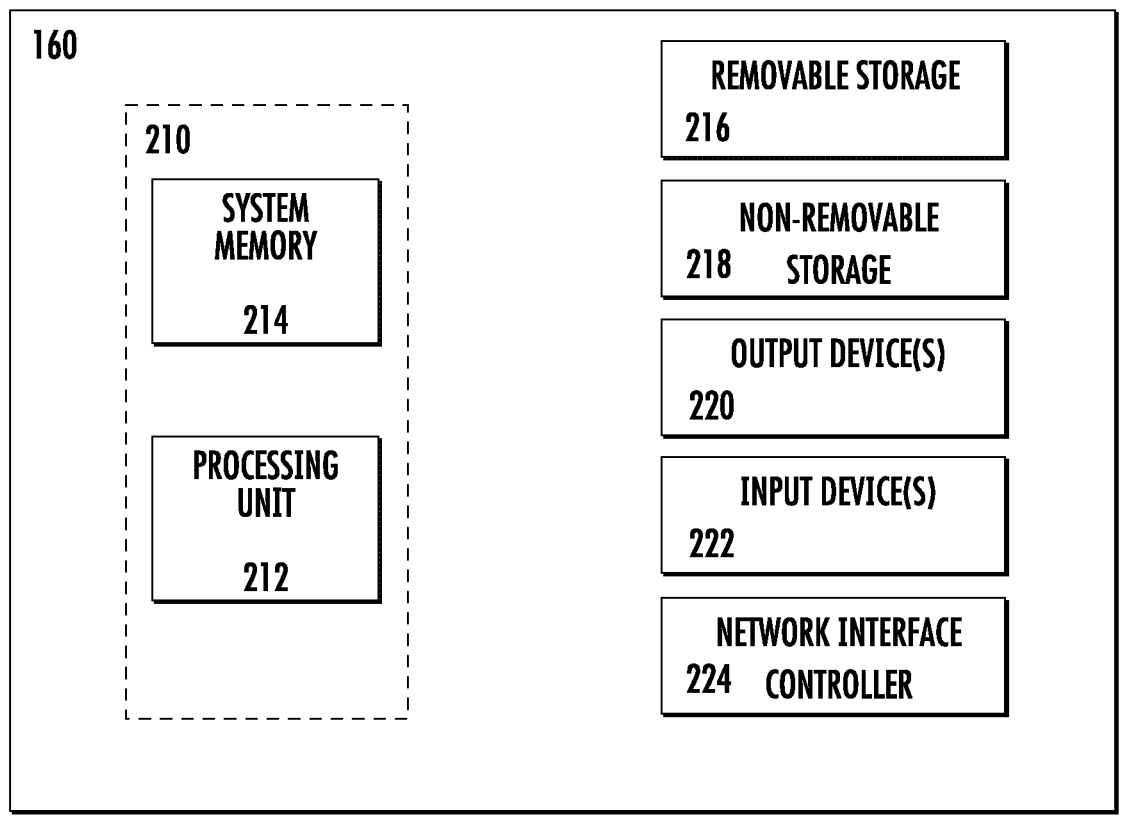
FIG. 30: Schematic of an exemplary computing device.

FIG. 30 illustrates an example computing device upon which examples disclosed herein may be implemented. The computing device (160) can include a bus or other communication mechanism for communicating information among various components of the computing device (160). In its most basic configuration, computing device (160) typically includes at least one processing unit (212) (a processor) and system memory (214). Depending on the exact configuration and type of computing device, system memory (214) may be volatile (such as random access memory (RAM)), non-volatile (such as read-only memory (ROM), flash memory, etc.), or some combination of the two. This most basic configuration is illustrated in FIG. 30 by a dashed line (210). The processing unit (212) may be a standard programmable processor that performs arithmetic and logic operations necessary for operation of the computing device (160).

The computing device (160) can have additional features/functionality. For example, computing device (160) may include additional storage such as removable storage (216) and non-removable storage (218) including, but not limited to, magnetic or optical disks or tapes. The computing device (160) can also contain network connection(s) (224) that allow the device to communicate with other devices. The computing device (160) can also have input device(s) (222) such as a keyboard, mouse, touch screen, antenna or other systems. Output device(s) (220) such as a display, speakers, printer, etc. may also be included. The additional devices can be connected to the bus in order to facilitate communication of data among the components of the computing device (160).

The processing unit (212) can be configured to execute program code encoded in tangible, computer-readable media. Computer-readable media refers to any media that is capable of providing data that causes the computing device (160) (i.e., a machine) to operate in a particular fashion. Various computer-readable media can be utilized to provide instructions to the processing unit (212) for execution. Common forms of computer-readable media include, for example, magnetic media, optical media, physical media, memory chips or cartridges, a carrier wave, or any other medium from which a computer can read. Example computer-readable media can include, but is not limited to, volatile media, non-volatile media and transmission media. Volatile and non-volatile media can be implemented in any method or technology for storage of information such as computer readable instructions, data structures, program modules or other data and common forms are discussed in detail below. Transmission media can include coaxial cables, copper wires and/or fiber optic cables, as well as acoustic or light waves, such as those generated during radio-wave and infra-red data communication. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit (212) can execute program code stored in the system memory (214). For example, the bus can carry data to the system memory (214), from which the processing unit (212) receives and executes instructions. The data received by the system memory (214) can optionally be stored on the removable storage (216) or the non-removable storage (218) before or after execution by the processing unit (212).

The computing device (160) typically includes a variety of computer-readable media. Computer-readable media can be any available media that can be accessed by device (160) and includes both volatile and non-volatile media, removable and non-removable media. Computer storage media include volatile and non-volatile, and removable and non-removable media implemented in any method or technology for storage of information such as computer readable instructions, data structures, program modules or other data. System memory (214), removable storage (216), and non-removable storage (218) are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device (160). Any such computer storage media can be part of computing device (160).

It should be understood that the various techniques described herein can be implemented in connection with hardware or software or, where appropriate, with a combination thereof. Thus, the methods, systems, and associated signal processing of the presently disclosed subject matter, or certain aspects or portions thereof, can take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs can implement or utilize the processes described in connection with the presently disclosed subject matter, e.g., through the use of an application programming interface (API), reusable controls, or the like. Such programs can be implemented in a high level procedural or object-oriented programming language to communicate with a computer system. However, the program(s) can be implemented in assembly or machine language, if desired. In any case, the language can be a compiled or interpreted language and it may be combined with hardware implementations.

Also disclosed herein are methods for selecting a cancer treatment regimen for a subject. The method can involve an in vitro microfluidic dose-response assay of a sample from a cancer of a subject to identify the response to an anticancer agent, such as a chemotherapeutic agent, compared to a control. The assay can involve the use of an observation chamber for visualizing cancer cells from the sample during the method. In some embodiments, the chemotherapeutic agent is diffused from one reservoir of a microfluidic chamber to the other thereby creating a stable gradient across the observation chamber. In some embodiments, cells are imaged continuously, allowing for the effect of time to be assessed.

In some examples, the method can further involve identifying cell death induced by the drug. Typical membrane-impermeable probes for detection of cell death, such as EthD-1, present a significant variation in the time for fluorescence acquisition after death in cell lines or patient samples. To avoid this confounding effect, disclosed is an approach that identifies cell death based of motion of the membrane. In some embodiments, the identification of cell death comprises: (a) collecting a first bright field image of a cancer cell at a first time; (b) collecting a second bright field image of a cancer cell at a second time; (c) applying an algorithm to the first and second images to identify the presence or absence of cell membrane motion; wherein the absence of cell membrane motion indicates cell death. Typical cell viability assays are often destructive or cytotoxic, if carried for long periods of time, limiting the information acquired in the temporal dimension. In the disclosed system and method, cancer cells, stroma and matrix do not have to be separated, and no cytotoxic agents have to be used to determine cell viability, thus allowing longitudinal studies of drug activity without interfering with the microenvironment. In some embodiments, only bright field imaging is used, thereby eliminating any toxicity from viability markers.

In some embodiments, the in vitro microfluidic dose-response assay comprises a combination of primary cancer cells from the sample, extracellular matrix, subject-derived stroma, and one or more growth factors. The extracellular matrix and stroma are components of chemoresistance in many tumors. However, the inclusion of these elements significantly increases the complexity of dose response assays, often requiring the separation between cancer and stromal cells, by matrix digestion and/or flow sorting (Misund K, Baranowska K A, et al. J Biomol Screen 2013; 18:637-46). Cell adhesion mediated drug resistance (CAMDR) is believed to be a cause of minimal residual disease in multiple myeloma (Meads M B, Gatenby R A, Dalton W S. Nat Rev Cancer 2009; 9:665-74). In some embodiments, the assay allows for assessment of environment-mediated drug resistance.

In cancers such as MM, where a few million cells are obtainable per patient biopsy, it is important to minimize the number of cells per experimental condition. In some embodiments, less than 20,000 cancer cells are used in the assay described herein (for example, less than 20,000; 15,000; 10,000; 5,000 or 2,000 cells). In some embodiments, more than 1,000 cells are used in the assay (for example, at least 1,000; 2,000; 3,000; 4,000; 5,000; 6,000, 7,000; 8,000; 9,000; or 10,000 cells). In some embodiments, 1,000-10,000 cells are used in the assay (for example, at least 1,000; 2,000; 3,000; 4,000; 5,000; 6,000, 7,000; 8,000; 9,000 or 10,000 cells).

The disclosed system and method can further involve collecting parameters from the assay to generate a multi-parameter model that summarized the response of the subject to the drug treatment. These parameters include, for example, drug concentration, exposure time, IC50, EC50, and drug free doubling time. Computational methods, such as those disclosed herein, may be parameterized by data from the disclosed method and used to estimate response to treatment with the drug being tested.

The disclosed system and method can be used to select a cancer treatment regimen for the subject based on the results of the multi-parameter model. In some embodiments, the integration between in vitro and in silico computational models allows for assessment of initial response to a drug. In some embodiments, the integration between in vitro and computational models allows for assessment of the progression-free survival.

In some embodiments, the cancer is a hematological malignancy. In some embodiments, the sample is a bone marrow aspiration. In some embodiments, the cancer is multiple myeloma.

The disclosed method may be used to identify drug candidates for any cancer type or subtype. A representative but non-limiting list of cancers include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers (e.g., leukemia); testicular cancer; rectal cancers, prostatic cancer, and pancreatic cancer.

In some embodiments, combinations of drugs are tested. In some cases, the dosing schedule of a combination of drugs is tested. In some embodiments, the heterogeneity of drug response is assessed. In some embodiments, the drug comprises melphalan, bortezomib, FAM-HYD-1 or combinations thereof.

EXAMPLES

Example 1

Materials and Methods

Cell lines. The human myeloma cell lines used were RPMI-8226, HS-5/GFP-labeled, NCI-H929 and 8226/LR-5. The 8226/dsRed2 cell line was stably transfected with the fluorescent protein dsRed2. All cells were maintained in culture with RPMI 1640 (Gibco) media supplemented with 10% heat inactivated fetal bovine serum (Life Technologies) and 1% penicillin-streptomycin solution (Invitrogen), in incubators at 5% $CO_2$, 37° C. Melphalan-resistant 8226/LR-5 cells were maintained in 5 µM melphalan in medium, and cultured in drug-free medium for 2 weeks prior to experiments.

Primary cancer cells. The in vitro response of cancer cells from 7 MM patients were investigated. The medical records were de-identified and only the following clinical-relevant information was reviewed: (A) treatment administered (chemotherapeutic agents, doses and schedule) prior to biopsy; (B) cytogenetics; (C) blood and urine electrophoresis results. Patients received standard-of care treatment, and consented to provide an extra sample of bone marrow aspirate during a routine biopsy. These aspirates were used in the in vitro assays further described. After informed written consent, bone marrow aspirates were obtained from multiple myeloma patients either newly diagnosed or with refractory disease. Processing of bone marrow aspirate and selection of MM cells is described below. MM cells were seeded into the Ibidi µ-slide Chemotaxis 3D device under experimental culture conditions (described below) within 4 hours of each patient biopsy.

Processing of bone marrow aspirates. Clinical bone marrow aspirates (20 mL) from patients were collected in sodium heparin syringe, and mononuclear cells were immediately isolated by centrifuging diluted marrow (1:1 with sterile PBS) over a Ficoll-Paque Plus (Amersham Biosciences) gradient at 400×g for 30 minutes at ambient temperature. The interface was removed, cells washed with cold PBS and counted. One cytospin slide was prepared and stained with Wright-Giemsa stain to assess plasma cell percentage. The amount of CD138 beads (Miltenyi cat #130-051-301) used were according to number of cells and plasma cell percentage. If starting sample was less than 20% plasma cells, the cells were resuspended using 90 µl separation buffer and 10 µl CD138 beads were added per $5 \times 10^6$ cells. If starting sample is more than 20% plasma cells, the cells were resuspended using 80 µl separation buffer and 20 µl CD138 beads per $1 \times 10^7$ cells. After a 15 minute incubation with beads at 4° C., the cells were passed through a 35 µm strainer added to pre-wetted LS columns (Miltenyi cat #130-042-401) placed in a magnetic field (Miltenyi Midi-MACS magnet). The column was washed 3 times and collected before removing from magnet and eluting CD138 enriched cells with 1 ml of separation buffer. CD 138 enrichment was assessed with another stained cytospin slide. Serum from each patient was filtered with a 0.22 micron syringe filter and was used to make supplemented RPMI1640 growth media with 10% heat inactivated fetal bovine serum, 10% patient serum, 1% penicillin-streptomycin.

Drugs. The following chemotherapeutic agents were tested: bortezomib (Selleckchem), melphalan (Sigma), and FAM-HYD-1.

In vitro dose response assays in 3D microfluidic chambers. Commercially available 3D cell culture slides (µ-slide Chemotaxis 3D Ibitreat from Ibidi, LLC) were gas and temperature equilibrated at 37° C., 5% $CO_2$ overnight prior to cell seeding. Each slide is comprised of three separate chambers each with a 1 mm wide, 50 µm high cell-viewing chamber that holds a volume of 6 µL. It is connected to two 65 µL reservoirs along both sides. Linear chemical gradients form across the cell chamber via passive diffusion. Aliquots consisting of 6.67 µL 10×MEM (Life Technologies), 6.67 µL deionized $H_2O$, 3.33 µL 7.5% sodium bicarbonate solution (Life Technologies), and 16.67 µL 1×RPMI 1640 (Life Technologies), were premixed and stored at 4° C. prior to experiments, as per manufacturer (Ibidi) instructions. 50 µL of 3.1 mg/mL Bovine collagen type I (Advanced BioMatrix) was added at time of seeding. 16.67 µL of cells suspended in RPMI 1640 were mixed into the collagen/media mix to a final volume of 100 µL in 1.5 mg/mL bovine collagen I (6-fold dilution of RPMI 1640 cell suspension). 6 µL of this cell/matrix mix were used to load each viewing chamber. For cell lines in single culture or mixed culture, the final concentration of cells was $3 \times 10^6$ myeloma cells/mL. For patient primary cells, the densities were $7 \times 10^6$ cells/mL for MM (CD138+), and $1 \times 10^6$ cells/mL for mesenchymal cells. These cell densities were optimized to better reflect physiological cell density, and maximize the number of cells in the observation chamber, while still maintaining enough separation to allow the individual identification of cells. Cell lines were seeded at lower density to account for their larger size and faster replication. The interval between mixing collagen with cells and media, and seeding the chambers was kept below five minutes at ambient temperature to minimize collagen polymerization. After seeding, an additional 15 minutes at room temperature allowed adherent cells (HS-5 or patient stroma) to sink to the bottom of the 3D chamber and keep the same focal plane for subsequent live imaging. Slides were then incubated at 37° C., 5% $CO_2$ for 1 hour. Collagen polymerization was checked by visual inspection of fiber formation on an inverted phase contrast microscope with a 20× objective lens. After gelation, reservoirs on each side of the slide were filled with 65 µL culture media. 16.25 µL of 4× drug in culture media was dropped onto a filling port on the left reservoir and then an equal volume was immediately drawn out of the other filling port. Slides were then placed into incubator for live imaging. For each experiment, there was a control with no drug added, which was used to detect spontaneous cell death. For single culture experiments, chemotherapy was added 2-4 h after cell seeding. For co-culture experiments with adherent stroma (HS-5 or patient stroma), drugs were added 24 h later to ensure stroma adhesion.

Continuous versus pulsed exposure. In experiments with continuous exposure, the drug was maintained in media for the duration of the experiment. If this duration exceeded 48 h, the media on both reservoirs was completely removed, and replaced by fresh media, to which drug was added as previously described (16.25 mL at 4× concentration). In pulsed exposure experiments, the media on both reservoirs was completely removed, and replaced by fresh media at the end of the pulsed exposure.

Image acquisition. Two different models of fluorescence microscopes were used for the experiments described herein: the first, JULI (Digital Bio), is a portable fluorescence microscope with bright field and red fluorescence capacities (ex/em 630 nm/660 nm), which was maintained inside a standard incubator for the duration of the experiments. The second platform was the EVOS FL (AMG), a bench top fluorescence microscope (red channel ex/em 531 nm/593 nm), which used a stage-top heating stage/incubator (Ibidi), which maintained the cells at 37° C., 5% $CO_2$, and 80% humidity. For the experiments here described, images were acquired every 5-minute intervals. In experiments where the red fluorescent 8226/dsRed2 cell line was tested, or the cell-death molecular probe ethidium homodimer-1 (EthD-1) was used, both bright field and red fluorescent channels were imaged, the first for changes in cell morphology and membrane motion, and the second for loss of innate fluorescence or activity of EthD-1, respectively.

Quantification of drug concentration over time within microfluidic device. In order to quantify the shape and stability of the drug gradient in the microfluidic device, a fluorophore-conjugated of the peptide HYD-1 (1.5 kDa) was used within the dose-response assay, a 3D gel matrix consisting of 1.5 mg/ml bovine collagen I with RPMI1640/MEM media was placed into the culture chamber of the Ibidi microfluidics device. After 45 minutes incubation at 37° C., reservoirs were filled with RPMI1640 media 10% heat inactivated FBS, 1% penicillin-streptomycin. FAM-HYD1 was diluted into media before replacing ¼th of the volume in the left reservoir with fluorescent drug solution (¹/₁₀ of stock). Fluorescence within the culture chamber was imaged in an EVOS FL microscope using the GFP filter (ex/em 470 nm/525 nm, 5× objective) with heated stage and gas incubation (37° C., 5% $CO_2$). Images were acquired at 1-minute intervals for 24 hours.

Digital image analysis. With a stable drug gradient established across the main channel of the microfluidic slide, the observation channel was divided into five sections, or regions of interest (ROI), each with an average drug concentration of 100%, 80%, 60%, 40% and 20% of the concentration in the drug reservoir, respectively. Sectioning the channel into five areas was a compromise between a minimum number of cells in each area, and the rounding due to the averaging of the drug concentrations across each section. Dose response was quantified with a macro developed for the software ImageJ, further described. As discussed below, membrane-impermeable probes for detection of cell death, such as EthD-1, present a significant variation in the time for fluorescence acquisition after death in cell lines or patient samples. To avoid this confounding effect, an approach that identifies cell death based of motion of the membrane was developed, described below.

Assessment of cell viability through membrane motion detection. It was observed that, although it was not possible to clearly discern a dead from a live cell based on the morphology in the bright field of a single image, all live cells suspended within the collagen matrix had observable membrane motion or shape changes, between two images taken in a 5-minute interval. These morphological changes abruptly stopped prior to cell death, indicating that this feature could be exploited as a marker for cell death. A macro for the open source software ImageJ was created using the plugins TurboReg (Thevenaz P, Ruttimann U E, Unser M. IEEE Trans Image Process 1998; 7:27-41) and RunningZProjector. The macro quantifies the amount of cell membrane motion in the different regions of interest, and writes a file with this information for each frame, or time point. Briefly, the macro loads the stack of bright field images taken at 5-minute intervals, and aligns them using the plugin TurboReg. This action removes translational motion, such as sliding of the microfluidic chamber, as well as vibration. Next, the native ImageJ "background subtraction" function was used with parameters "rolling ball radius=1 pixel" and "sliding parabolic" (Sternberg S R. Biomedical Image Processing. Computer 1983; 16:22-34). Background subtraction served to normalize image sequences across different experiments and/or microscopes used to image the chambers, making cells appear as bright spots against a uniform dark background. Motion and small variations in cell membranes were detected using the plugin RunningZProjector. It detects the maximum pixel intensity across a 6-frame/slice interval, corresponding to 30 minutes. The original image was then subtracted from the maximum pixel intensity projection, resulting in an image where actively moving membranes appear as bright rings. ImageJ's "Gaussian blur" filter was used to convert these bright rings into spots that cover the entire cell, and produce overlaid images.

Validation of motion detection algorithm through fluorescence. Different fluorescent-labeling agents for cell viability were tested as live-imaging approaches for response to chemotherapy. However, cytotoxicity, photo bleaching, intercellular variability of delay between cell death and signal detection, and incomplete representation of viable/apoptotic/necrotic cell states added noise to the assay. A multiple myeloma cell line was stably transfected with dsRed2 (8226/dsRed2), and used as a reference to visually detect the cytotoxic effect of drugs through loss of red fluorescence. RFP expression is an intrinsic marker for these cells: live cells will quickly lose fluorescence upon cell death due to membrane burst accompanied by release of cytoplasmic components, including the fluorescent protein.

Validation of motion detection algorithm through bioluminescence. NCI-H929 cells were seeded in 96-well plates in culture media or in a 3D collagen matrix with culture media added on top of the cell/collagen layer. In wells without collagen, 1.5×10$^5$ cells were resuspended in 504, of media for a final density of 3×10$^6$ cells/mL. To more closely resemble microfluidic assay conditions, 1.5×10$^5$ cells were suspended in 304, of 1.5 mg/mL collagen matrix and were left to polymerize at 37° C. for 1 hour. 20 µL of media was then added as a separate phase on top of the cell/collagen layer. Melphalan was serially diluted in 2-fold steps to a final concentration range of 100 µM to 1.56 µM in 7 rows. The same procedure was performed for bortezomib to final concentrations of 20 nM to 0.31 nM. All conditions and controls were performed in triplicate. After 24 hours of continuous drug exposure at 37° C. and 5% $CO_2$, 50 µL CellTiterGlo was added to each well and the plates were placed on an orbital shaker at room temperature for 10 minutes. 20 minutes later, bioluminescence was measured at ambient temperature on a microplate reader. Percent cell viability was defined as luminescence normalized to controls at 24 hours.

Analysis of Experimental Data.

The quantification of the dose response of the cells in the experiment used Matlab's (MathWorks) function Isqcurvefit, which finds the coefficients that minimize the distance between a function and a set of data points.

The default function of dose response was written as Equation 1, and the data points were the normalized viability in each region of interest (ROI) at a given time point and drug concentration:

$$\text{Viability}(\%) = 100 \times \frac{2^{\Delta T/T}}{\left(1 + \left(\frac{Rx}{IC_{50_{Rx}}}\right)^{expRx} \times \left(\frac{\Delta T}{IC_{50_{\Delta T}}}\right)^{expT}\right)} \quad \text{(Equation 1)}$$

The goodness of the fit was calculated from a linear regression of the points of the fit equation with the actual observed experimental points using Prism 5 (GraphPad) and quantifying the slope and $R^2$ of the regression. For each example, two hypotheses were tested: either the sample was composed of one or two sub-populations. When no significant differences were observed in $R^2$, the simplest model was used (one population).

Equation 1 is the simplest expression that describes how a homogenous population of MM cells responds to chemotherapy as a function of concentration and exposure time. A growth term was included in the numerator of Equation 1, where T is the doubling time, and $\Delta T$ is the variable representing drug exposure time. Rx represents the drug concentration to which cells are exposed, while $IC50_{Rx}$, $IC50_{\Delta T}$, expRx, and expT are constants that determine the drug concentration and exposure time that causes death of 50% of the MM cells, and the steepness of the slope of the viability curve, respectively.

The alkylating agent melphalan has a short half-life in media and in vivo of approximately 2 h, mainly due to hydrolysis (Samuels B L, Bitran J D. J Clin Oncol 1995; 13:1786-99). It was observed, however, that in long-term experiments, cells continue to die a week after melphalan exposure (see Results). For this class of drugs, a mathematical expression that encompasses drug half-life, DNA-damage, and DNA-damage-induced cell death was created (Equation 2).

$$Viab(\%) = 100 \times \text{Death} \times \text{Growth} \quad \text{(Equation 2)}$$

$$\text{Death} = \frac{1}{1 + \frac{CumulDamage^{expIC50}}{IC_{50}}}$$

$$CumulDamage(t + dt) = CumulDamage(t) + \left(\int Rx dt\right)^{expDMG}$$

$$\text{Growth}(t) = 2^{\frac{t}{T \times (1 + CumulDamage(t) \times K_T)}}$$

$$Rx(t) = Rx_o \times 2^{-\frac{t}{T_{Mel}}}$$

"Death" and "Growth" are the two functions that determine the changes in number of viable cells in a given drug concentration, at a certain time point. "Death" represents the probability that any given cell from a population will die as a function of accumulated DNA damage ("CumulDamage"), which in turn is proportional to the area under the curve (AUC) of drug concentration "Rx" and exposure time "dt". "expDMG" is an empirical exponent. "Growth" quantifies cell replication, which depends on the drug-free doubling time T, the amount of DNA damage "CumulDamage", and an empirical proportional constant KT. In other words, DNA damage slows replication (Gardner S N. Cancer Res 2000; 60:1417-25). The last expression means that the concentration of active melphalan in media, Rx, decays with a half-life TMel of 2 h.

Equation 2 is an empirical expression, with the goal of interpolating the data points across time and concentration dimensions, while recapitulating known mechanisms of melphalan toxicity and degradation. It is not, however, the only possible expression possible, and it may not properly compute the viability in concentrations or exposure times significantly higher than the experimental conditions.

Computational modeling of therapy. As a proof of principle, to exemplify the application of these in vitro chemosensitivity assays in estimating patient response to therapy, a computational model (Silva A S, Kam Y, et al. Cancer Res 2012) was used to simulate a hypothetical single-agent bortezomib regimen in an animal model (s.c. NCI-H929 in SCID mouse), and for four patients whose MM cells' sensitivity to bortezomib were tested in vitro.

In this computational model, one or more sub-populations are represented, each with a size, a doubling time, and a level of sensitivity to the chemotherapeutic agent tested. Carrying capacity, which is the maximum theoretical growth rate of the entire tumor burden, was estimated from the labeling index commonly observed in MM patients (~1-3%). Intratumoral competition was modeled by an equation that determines that bigger populations have higher chance of replicating than smaller ones (Equation 3), a dynamic similar to genetic drift.

$$N_i(t+dt) = N_i(t) \times \left(1 + \left(\frac{Rx}{IC50_{Rxi}}\right)^{expRXi} \times \left(\frac{dt}{IC50_{\Delta Ti}}\right)^{expTi}\right)^{-1} \times \left\{\left[(1+LI)^{\frac{dt}{Ti}} - 1\right] \times \frac{N_i(t)}{\sum N_j(t)} + 1\right\}$$ (Equation 3)

Equation 3 describes how the size of a sub-population within the tumor burden (NO changes within an interval of time (dt) in response of drug-induced cell death induced by exposure to a drug at the concentration Rx for the interval of time dt. The surviving cells may replicate at a rate determined by their labeling index (LI), the duration of their cell cycle (T), and the percentage that the sub-population represents in the total tumor burden.

Bortezomib concentration in blood is characterized by a peak of −100 nM, followed by a sharp decrease, and a stable concentration of ~1-3 nM between 2 and 192 h post IV administration (1.3 mg/m2) (Ogawa Y, Tobinai K, et al. Cancer Sci 2008; 99:140-4; Reece D E, Sullivan D, et al. Chemother Pharmacol 2011; 67:57-67). The in vitro chemosensitivity data from patients 8, 11, 12, and 13 parameterized the computational models of clinical response for each of these patients in a hypothetical single-agent bortezomib regimen, in which the bone marrow concentration would remain constant at 3 nM.

As a preliminary validation of the correlation between in vitro and in vivo chemosensitivity, computational models parameterized by assays with the human MM cell line NCI-H929 were used to estimate the response to bortezomib treatment of a sub-cutaneous mouse model, treated with 1 mg/kg bortezomib biweekly (Ishii T, Seike T, et al. Blood Cancer J 2012; 2:e68). Pharmacokinetic studies have shown that such IV injections in mice cause a peak blood concentration of ~0.5 nM, and ~0.4 nM at 48 h. For these simulations, a stable 0.4 nM concentration of bortezomib in the bone marrow of these mice along the treatment was considered. NCI-H929 cells have a cell cycle of approximately 24 h, and in the subcutaneous model the tumors have a doubling time of approximately 3.5 days, indicating that in this animal model, approximately 20% of H929 cells are actively replicating at a given time, which was used as labeling index in the simulations.

Results

Characterization of shape and duration of drug gradient. The first step of validating the in vitro platform was to determine the stability, and also the duration of any transients during the formation of the drug gradient across the observation chamber. For this purpose, a conjugate of the fluorescent molecule fluorescein (FAM) and the 1.5 kDa peptide HYD-1, an experimental drug with direct toxicity to MM cells (Nair R R, Emmons M F, et al. Mol Cancer Ther 2009; 8:2441-51), was used. Live imaging was used to quantify the fluorescence in images taken at 1-minute intervals during 18 h (FIG. 1). The fluorescent signal gradient was stable for the interval of the experiment, and the transient time for its formation was shorter than the period between drug injection in the slide and start of imaging (~5-10').

Figure 2:
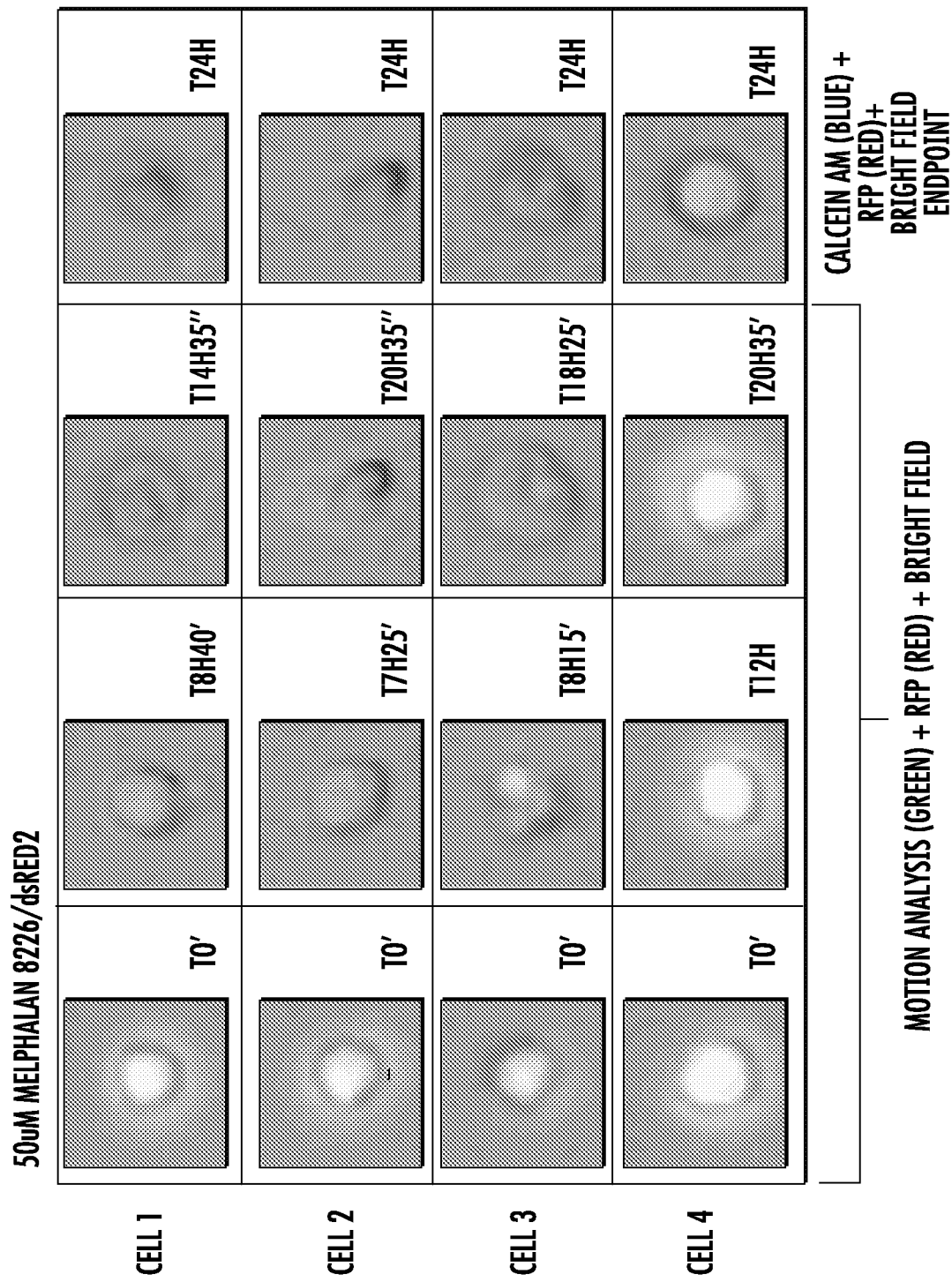
FIG. 2: Loss of membrane motion precedes loss of innate fluorescence in MM fluorescent cell line. The cell line RMPI-8226 was stably transfected with the fluorescent protein dsRed2. Upon death, cells stop producing the protein, which can degrade inside the cytoplasm and/or diffuse to media upon cell membrane bursting.
Figure 3:
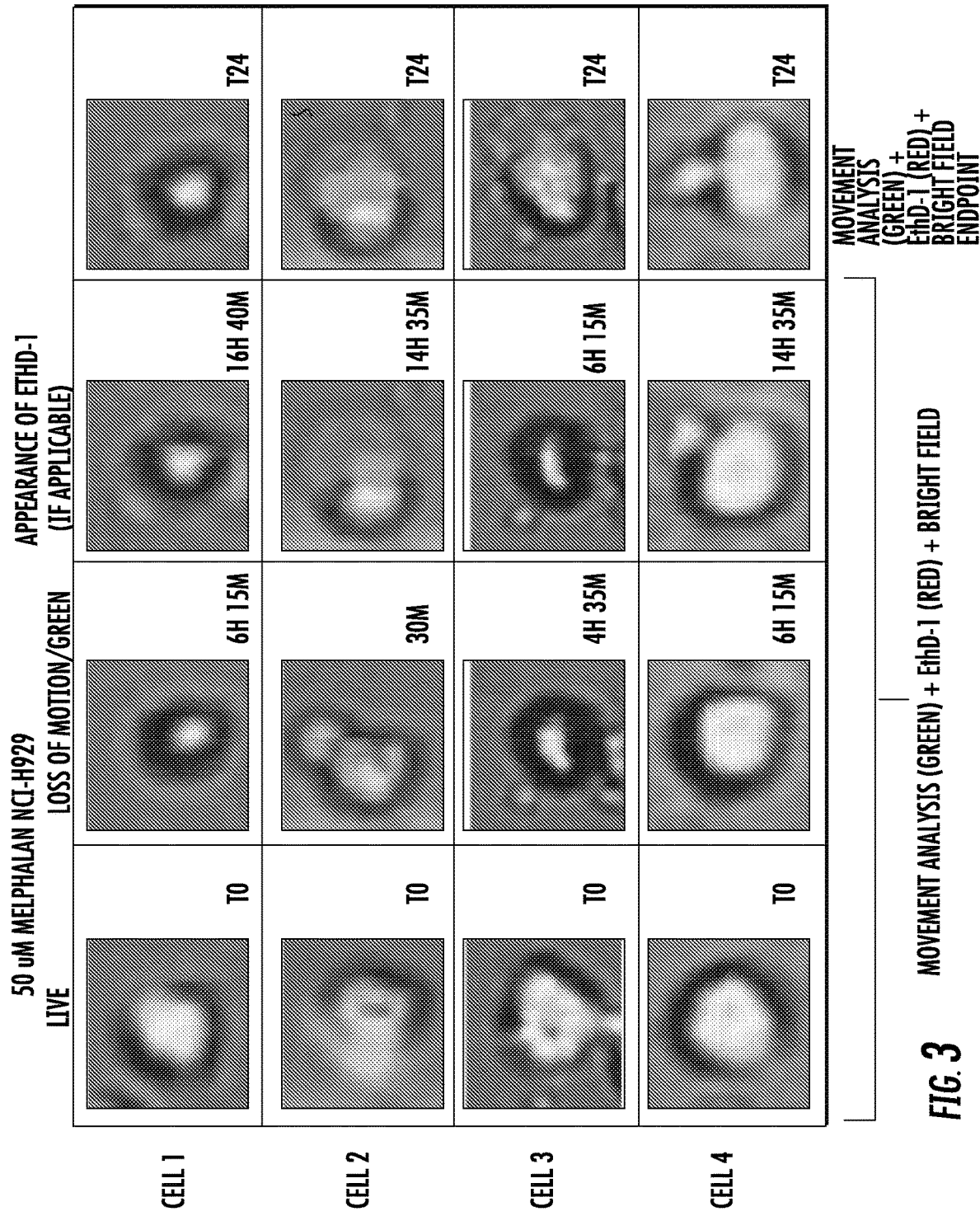
FIG. 3: Loss of membrane motion is an early event in cell death, preceding loss of membrane integrity.

Loss of membrane motion is a reliable maker of cell death. An algorithm for detection of cell membrane motion was used to detect cell death in patient primary cells, due to the significant variation of the delay between cell death and membrane permeabilization, and acquisition of fluorescence from molecular probes. FIG. 2 depicts the delay between the detection of cell death using the motion-detection algorithm, and loss of fluorescence in the stably transfected cell line 8226/dsRed2. FIG. 3 exemplifies the delay of acquisition of the molecular probe Ethidium homodimer-1 (EthD-1) red fluorescence in NCI-H929 cells.

Figure 4:
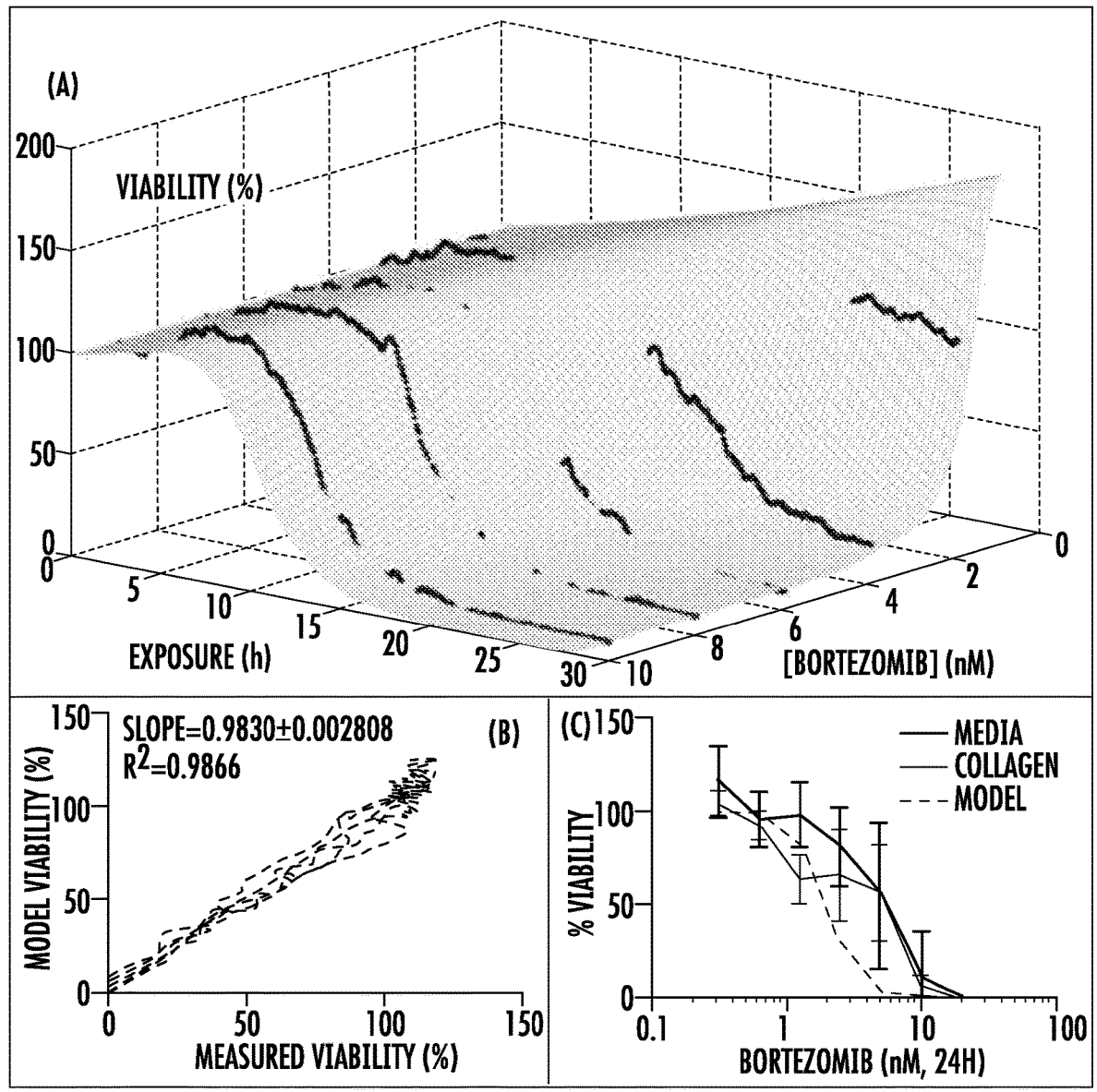
FIG. 4: Quantification of sensitivity of the human myeloma cell line NCI-H929 to the proteasome inhibitor bortezomib. The disclosed microfluidic assay was used to generate a series of measurements corresponding to cell viability at combination of exposure time and drug concentration. These data points in turn were fit to the mathematical expression of dose response, Equation 1. (A) Sensitivity of the human myeloma cell line to the proteasome inhibitor bortezomib. (B) Goodness of fit of the mathematical model to the 1,670 data points. (C) Comparison of viability measurements at 24 h between the mathematical model and a standard ATP-based bioluminescent assay, with NCI-H929 cells in suspension in media or in collagen, using a standard 96-well plate.

Effect of the proteasome inhibitor bortezomib. The cell line NCI-H929 was exposed to a stable gradient of bortezomib (maximum concentration 10 nM) for 24 h, and a dose-response surface was created (FIG. 4A). According to these results, the bortezomib concentration that would lead to a 50% reduction in the number of live cells after 24 h, compared to the initial time point, was approximately 2.5 nM. The concentration that would lead to a 50% reduction in the number of live cells, compared to the control at 24 h was approximately 1.9 nM. The same cell line was seeded in a 96-well plate, in suspension or in collagen, and cell viability was measured using the ATP-based assay CellTiter-Glo (FIG. 4C). The Pearson test produced "r" values of 0.8905 and 0.8704 (P values 0.003 and 0.0049) for the correlation between the model and suspension, and collagen results, respectively.

Figure 5:
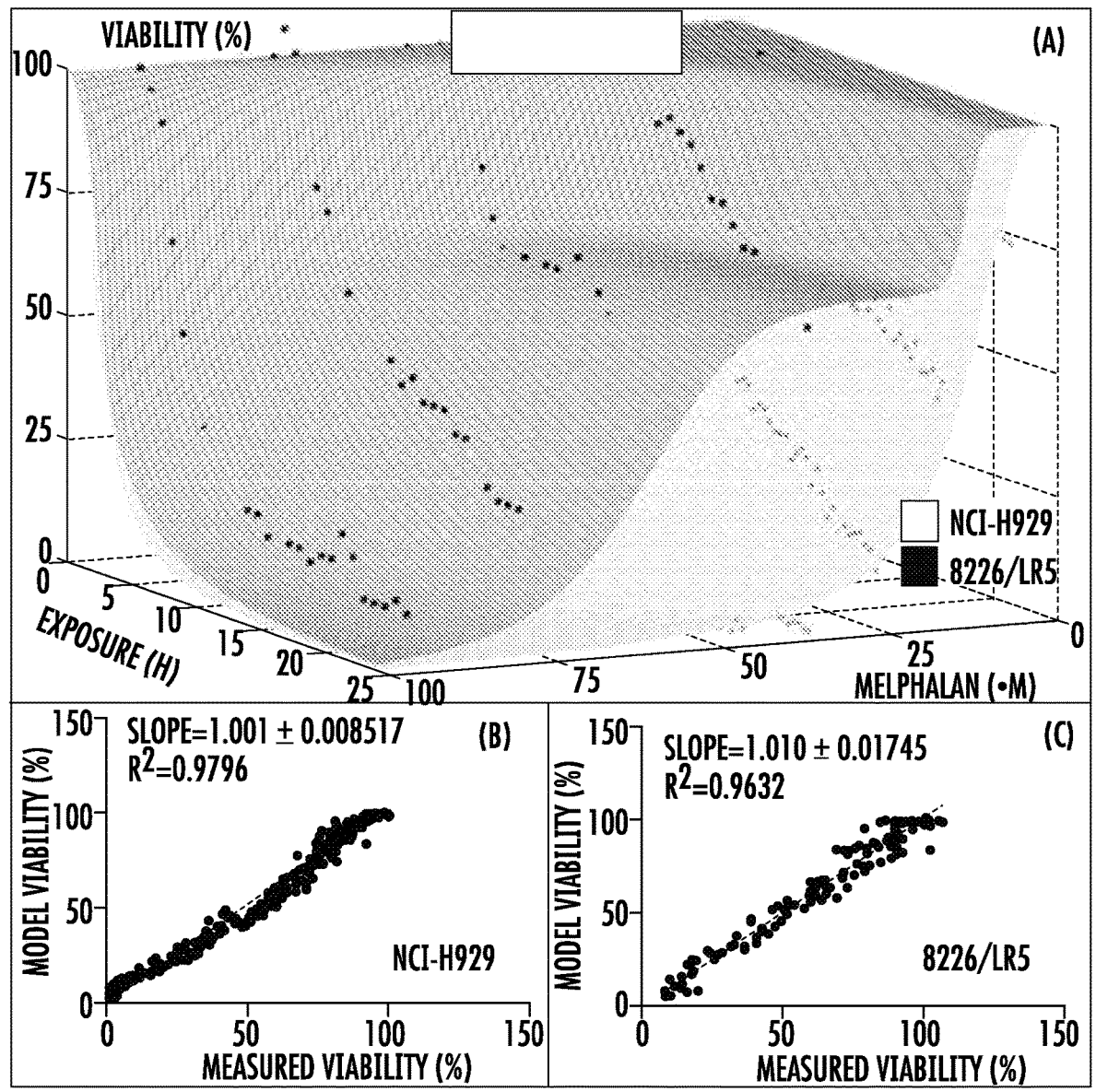
FIG. 5: Intrinsic chemoresistance to melphalan. The human MM cell lines 8226/LR5, selected by continuous exposure to melphalan, and NCI-H929 were exposed for a 24 h continuous stable of gradient of melphalan in the microfluidic chamber. While the cell line NCI-H929 was fit to a single population, the 8226/LR5 cell line was better fit by a two-population curve, with approximately 70% of resistant cells and 30% of sensitive. This result indicates that the loss of chemoresistance of 8226/LR5 cells in absence of melphalan might be due to heterogeneity in this population.
Figure 6:
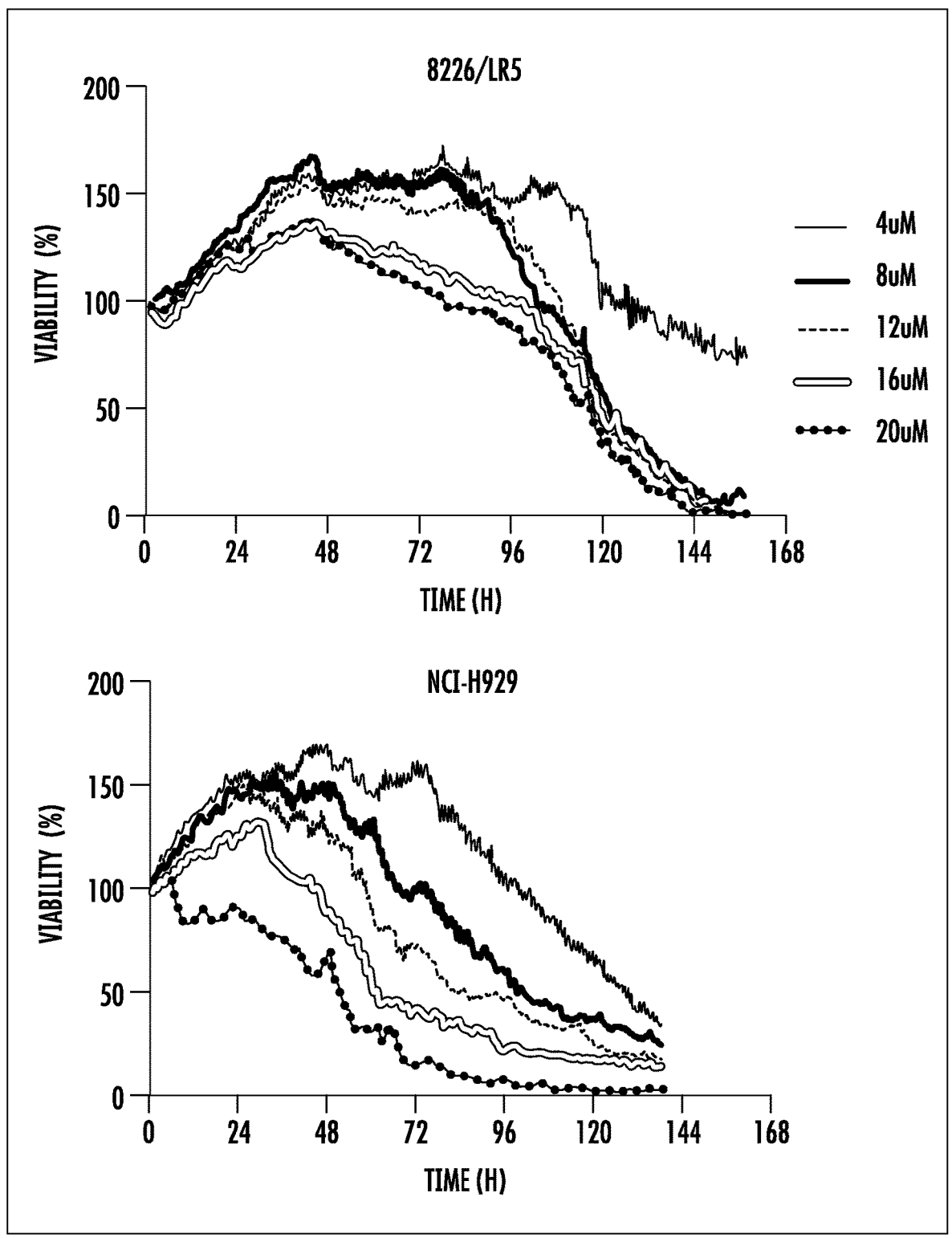
FIG. 6: The duration of melphalan toxicity post-withdrawal. 8226/LR5 (top) and NCI-H929 (bottom) cells were exposed to a melphalan gradient with highest concentration of 20 µM. Melphalan's half-life is approximately 1-2 h in media. At highest concentration, NCI-H929 cells began to die after 24 h, while 8226/LR5 viability began to decline at 36 h. Both cell lines continued dying for over a week. This delayed toxicity of melphalan was thus considered in the computational model for clinical response (Equation 2).

Quantification of melphalan innate resistance in cell lines in single culture. The melphalan sensitive and resistant cell lines NCI-H929 and 8226/LR5 were exposed to stable gradients of melphalan for 24 h (highest concentrations of 50 μM and 100 μM, respectively) and chemosensitivity was quantified. The analysis of 8226/LR5 detected a sub-population of sensitive cells (approximately 30%, FIG. 5A), indicating that this cell line is actually heterogeneous, a possible explanation for the loss of resistance commonly observed when these cells are maintained in melphalan-free medium for many weeks (Bellamy W T, Dalton W S, et al. Cancer Res 1991; 51:995-1002). Melphalan concentration that induced 50% of death in cells ($EC_{50}$) for 24 h continuous exposure was approximately 50 µM for 8226/LR5, and approximately 12 µM for H929. Long-term exposure to lower, more physiological doses (10-20 µM) of melphalan, however, indicated that, although all melphalan had been hydrolyzed in the first 24 h in media, cell death continued to occur after 6 days of drug exposure (FIG. 6).

Figure 7:
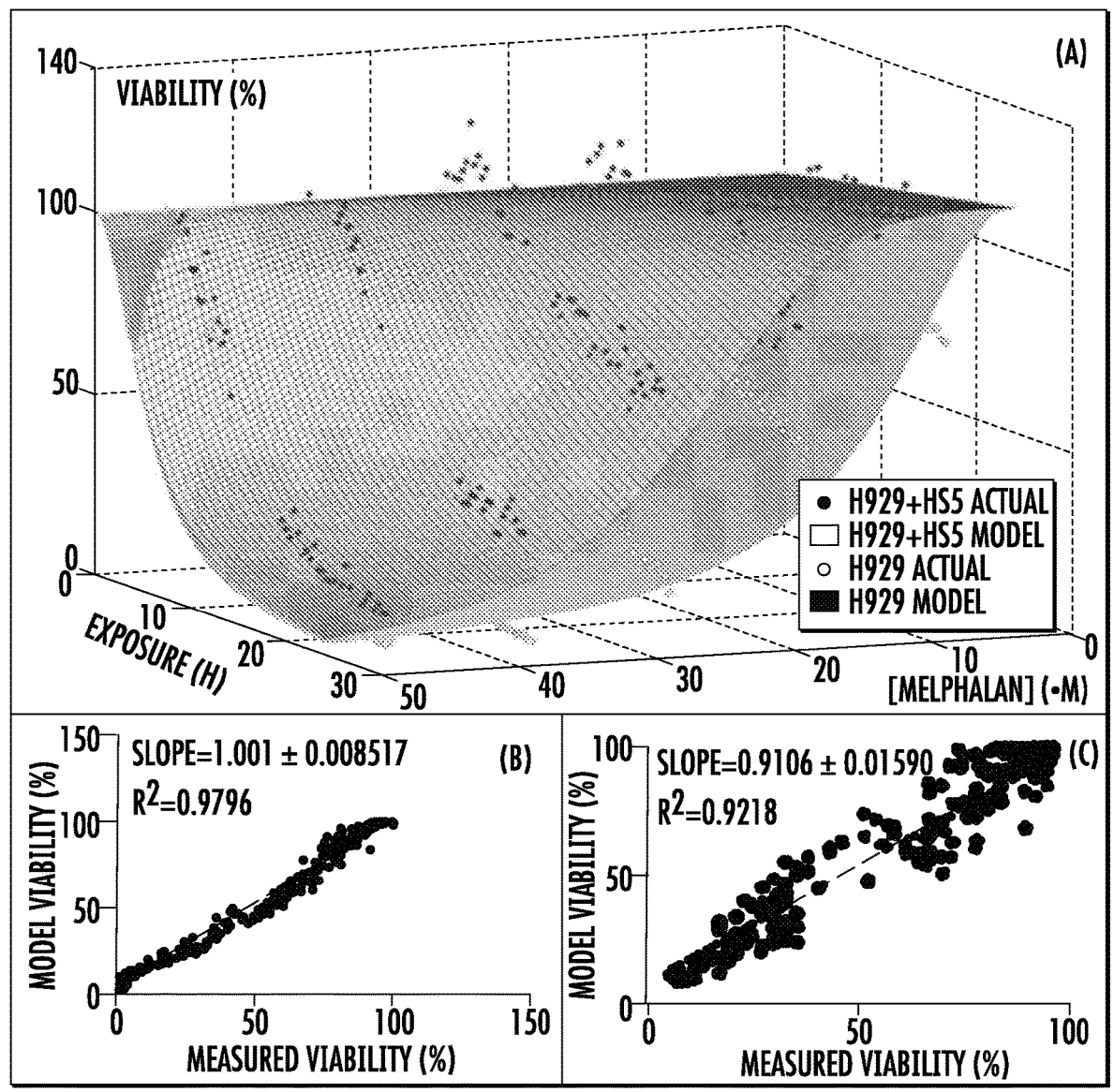
FIG. 7: Effect of Cell Adhesion Mediated Drug Resistance in the MM cell line NCI-H929 treated with melphalan. (Top) The co-culture of the NCI-H929 human MM cell line with the human bone marrow derived stromal cell line HS-5 confers increased resistance to melphalan. Melphalan concentration and exposure used to reduce viability in 50% (kR and kT, respectively) increase from 28 to 40 µM and 12 to 15 h, respectively. (Bottom) Linear regression of fit and actual experimental points for both experiments.

Quantification environment-mediated melphalan resistance. Cell adhesion mediated drug resistance (CAMDR) is believed to be a cause of minimal residual disease in multiple myeloma (Meads M B, Gatenby R A, Dalton W S. Nat Rev Cancer 2009; 9:665-74). This mechanism is caused by direct MM-stroma cell adhesion, by paracrine loops of soluble factor secretion, or MM-extracellular matrix adhesion. In order to quantify the importance of MM-stroma adhesion under physiological conditions (high density, in presence of ECM), the MM cell line NCI-H929 was co-cultured with the bone marrow derived stromal cell line HS-5/GFP. A significant shift towards resistance was observed at later time points (approximately 24 h), and was most expressive around the concentration of 20-30 µM (FIG. 7).

Figure 8:
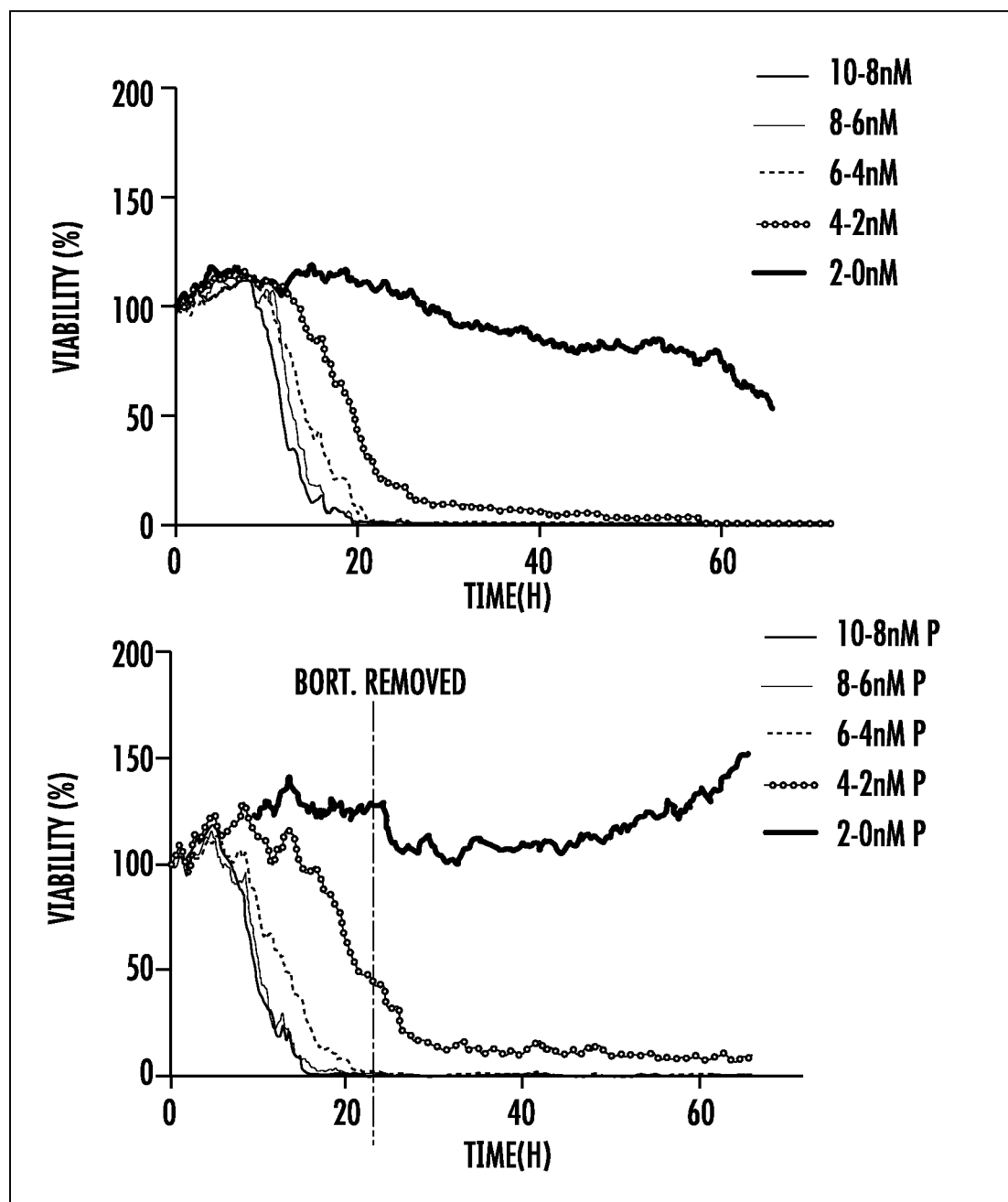
FIG. 8: The duration of bortezomib activity post-withdrawal. NCIH929 cells in two microfluidic chambers were exposed to a bortezomib gradient for 24 h. After 24 h, the media from both chambers were replaced. Drug was refreshed in the first chamber (top), while drug was removed from the second (bottom, P, for pulsed exposure). As shown in the 65 h-study, upon removal of bortezomib, cell death stops and cells resume growth. Same assay could be used to study lingering effects of experimental drugs with short half-lives.

Continuous versus pulsed exposure to drugs. To exemplify the study of continuous versus pulsed exposure to drugs, two chambers with NCI-H929 cells were exposed to bortezomib for 24 h. In one the medium was replaced by drug-free medium, while in the other fresh medium with bortezomib was added. Being a reversible proteasome inhibitor, the results suggest that bortezomib-induced death stops upon drug withdrawal (FIG. 8), unlike melphalan (FIG. 6).

Figure 9:
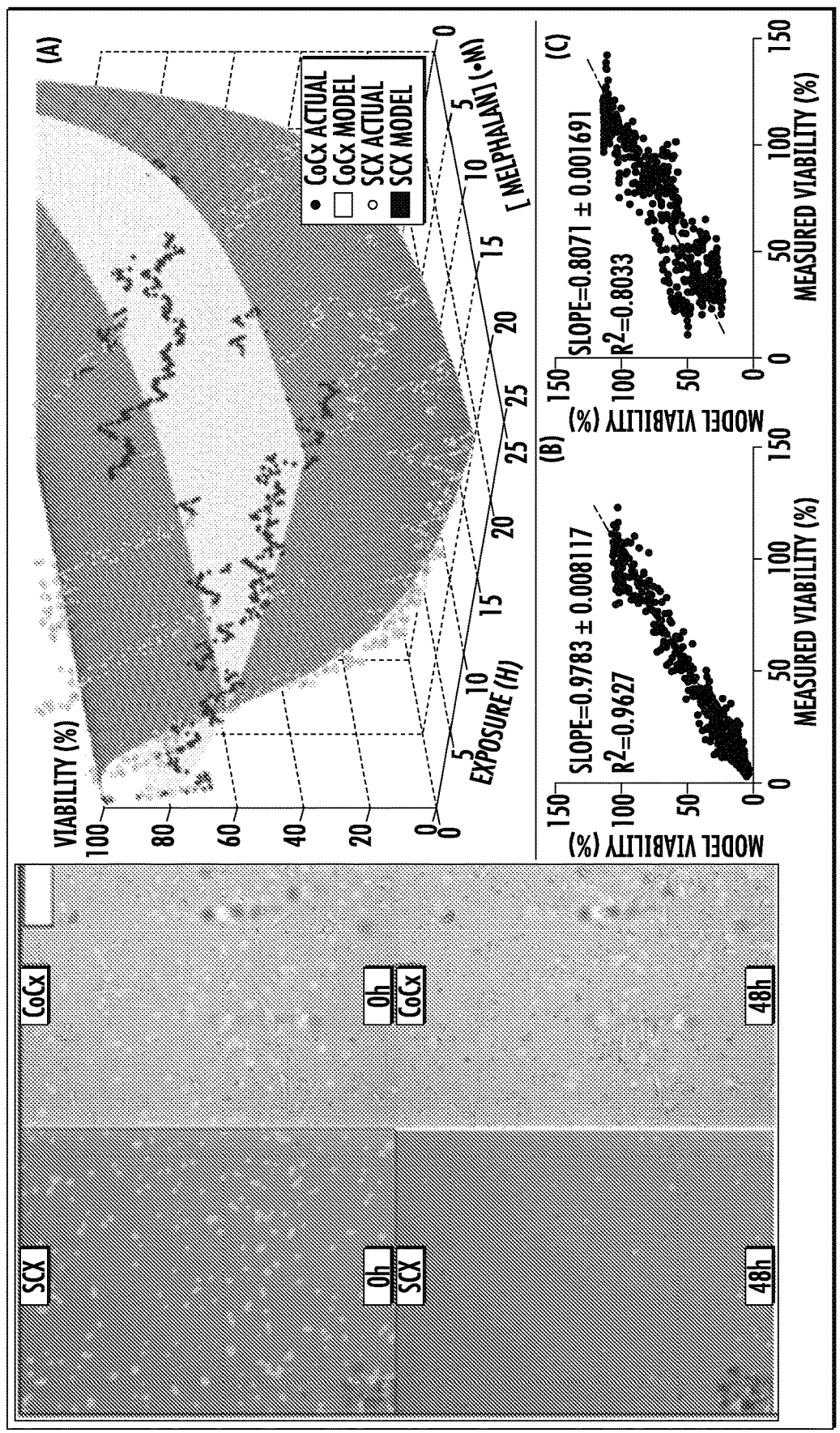
FIG. 9: Primary MM cells in co-culture with patient stroma are significantly more resistant to melphalan. Patient 14 was a newly diagnosed patient. MM cells were sorted (CD138+) from bone marrow aspirate, and seeded into microfluidic chamber in single (SCX, 0 h) or co-culture with patient stromal cells (CoCx, 0 h). Digital image analysis identified live cells and pseudo-colored them as green. A stable linear gradient of melphalan was established across observation channel: 25 µM on the left, 0 µM on the right, and cells were imaged every 5 minutes for 48 h. After 48 h, almost all MM cells were dead in single culture (SCX, 48 h), while a significant number of MM cells were still alive in co-culture with stroma (CoCx, 48 h). (A) Dose response surfaces built using measurements of viability in single (SCX) and co-culture (CoCx). (B) Goodness of fit of dose response surfaces (model) and actual data points for single culture, and (C) co-culture.
Figure 10:
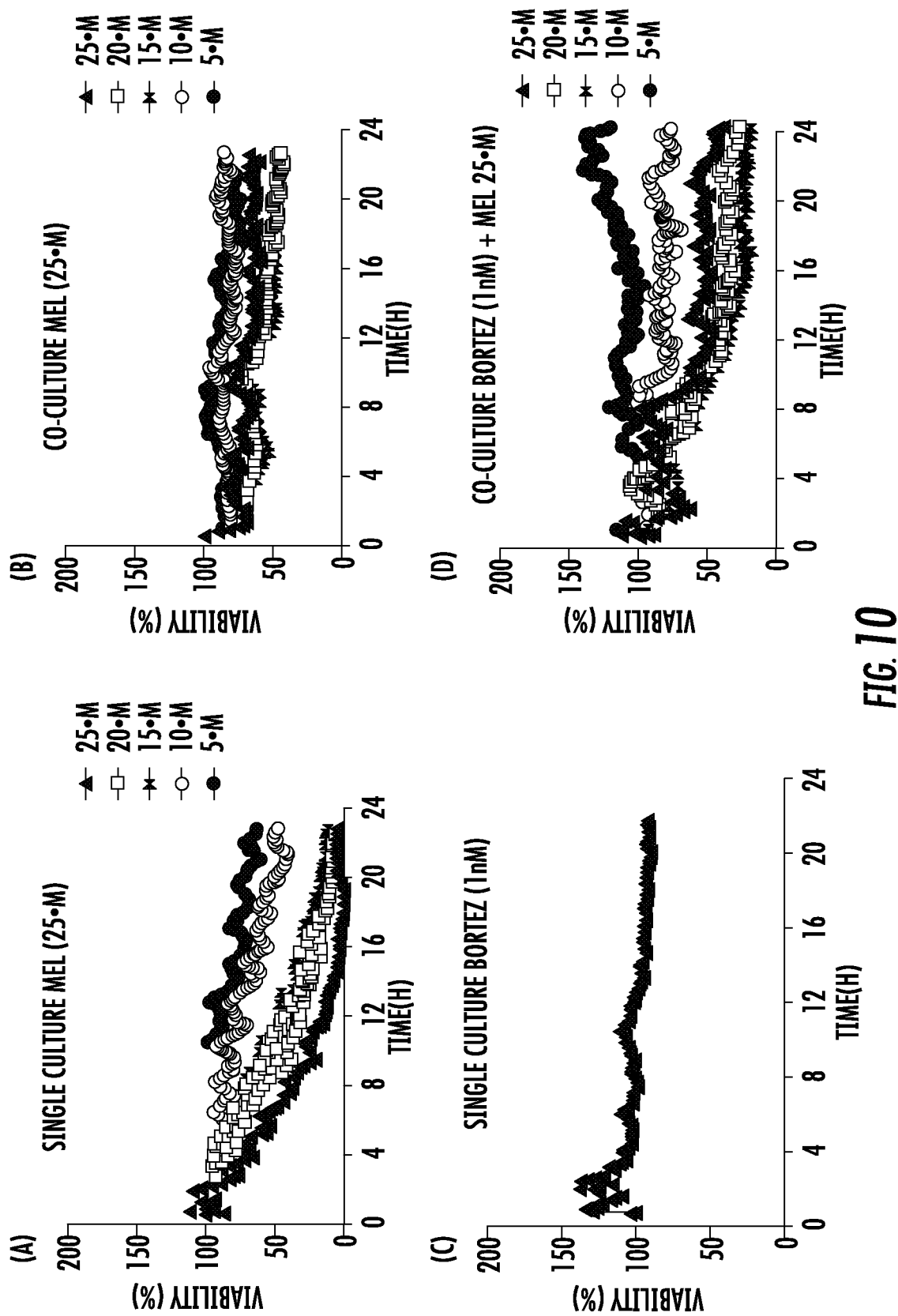
FIG. 10: Quantification of bortezomib-induced EMDR circumvention in primary MM cells. Patient 14 was a newly diagnosed patient. MM cells were sorted (CD138+) from bone marrow aspirate, and seeded into microfluidic chamber in single and co-culture with adherent stromal cells (CD138−). (A) In single culture, MM cells were significantly more sensitive than in co-culture (B). A dose-response assay with bortezomib indicated that 1 nM was the highest concentration that did not cause MM cell death (C) during the 24 h-period. By combining a stable gradient of melphalan, with a uniform concentration of bortezomib, the chemosensitive phenotype is restored in co-culture (D).

Melphalan chemosensitivity of primary MM cells in single and co-culture. From the 17 patient samples obtained so far in this protocol, the first 10 were used for development and optimization of the platform. The results of the 7 others are here described. CD138+ sorted primary MM cells from patient 14, a newly diagnosed patient, were exposed for 48 h to a stable gradient of 25 µM melphalan in single and co-culture, with patient-derived stroma. As shown in FIG. 9, adhesion to stroma significantly increased the survival of MM cells, shifting the 48 h $EC_{50}$ from 2 µM in single culture to 12 µM in co-culture. This effect could be circumvented by combination of a proteasome inhibitor at sub-lethal levels (Yanamandra N, Colaco N M, et al. Clin Cancer Res 2006; 12:591-9) (FIG. 10).

Figure 11:
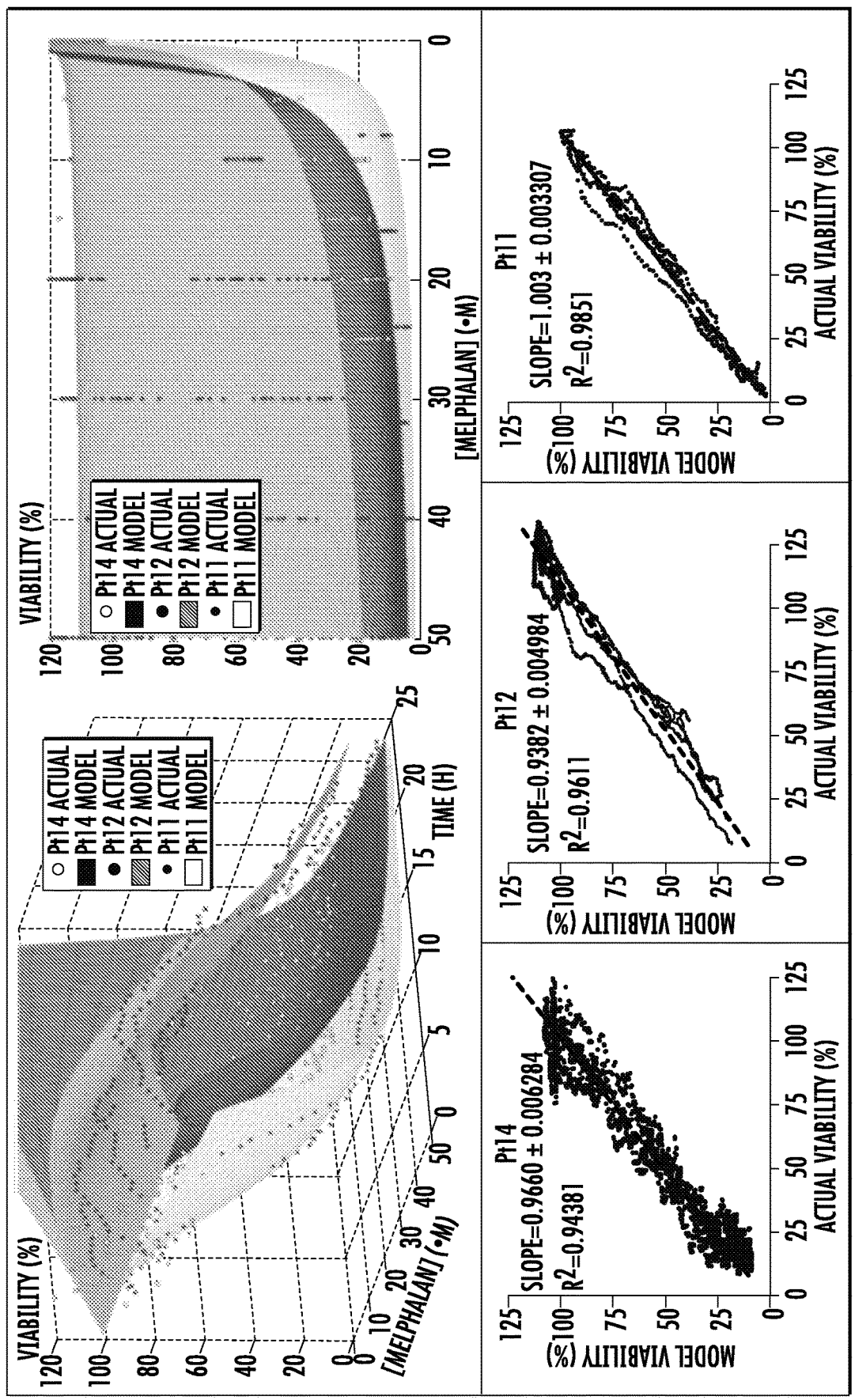
FIG. 11: In vitro melphalan chemosensitivity of three MM patients. Patient 14 was a newly diagnosed/high-risk patient, patient 12 was a relapsed/standard risk patient previously treated with high-dose melphalan and bone marrow transplantation. Patient 11 was a smoldering/standard-risk patient. In all three assays, cells were seeded in single culture in 3D collagen matrix with patient plasma supplemented medium. (Top, left) After 24 h continuous exposure to a stable melphalan gradient ranging from 0 to 50 µM, cells from the three patients responded at different rates, with patient 12 being the most resistant, and patient 11 the most sensitive. While the $EC_{50}$ for 24 h (Top, right) was approximately 4 µM for patients 12 and 14, and approximately 1 µM for patient 11, the $EC_{20}$, for example, was significantly higher in the relapsed patient: 50 µM for patient 12, 10 µM for patient 14, and approximately 3 µM for patient 11.
Figure 12:
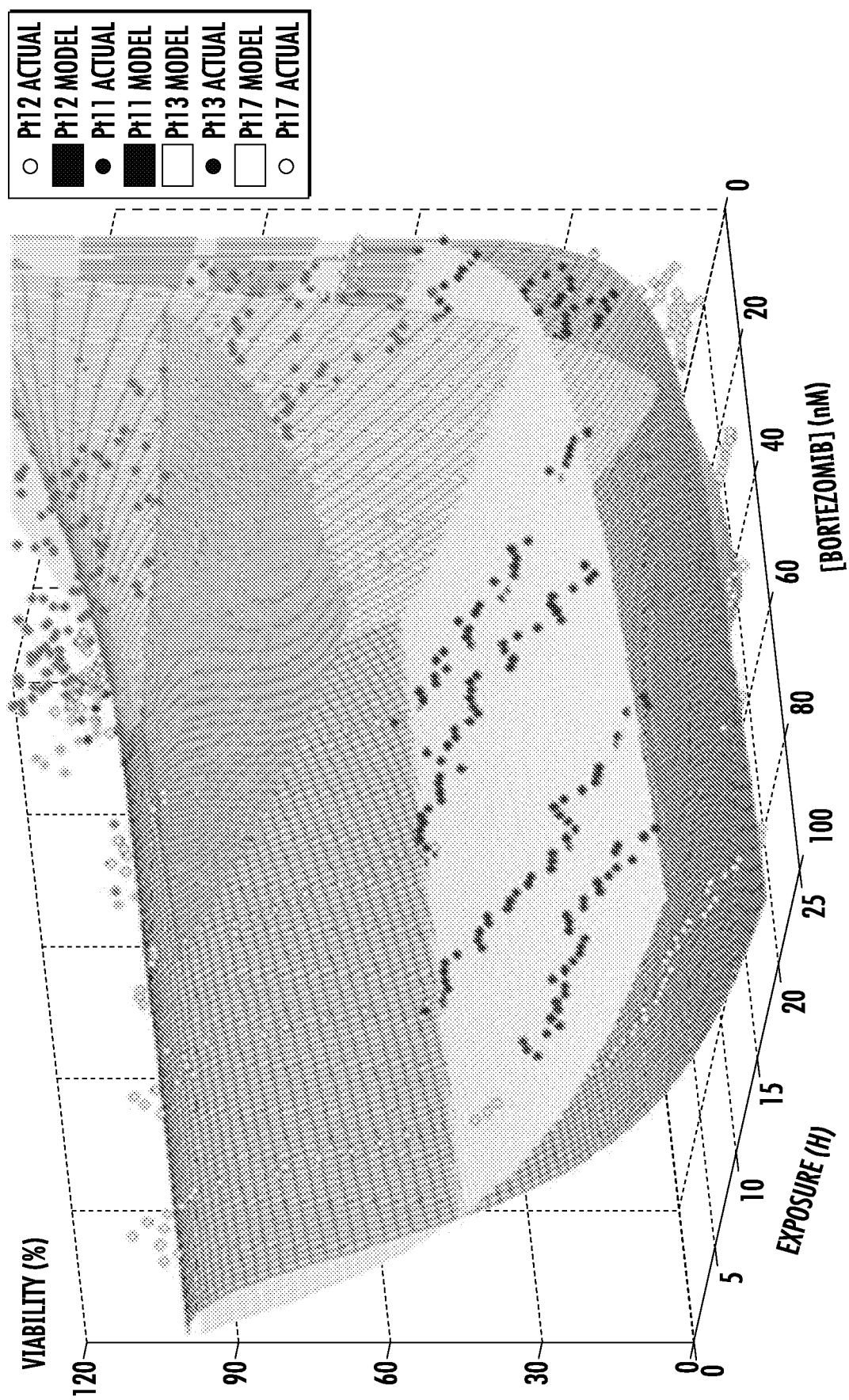
FIG. 12: In vitro response of primary MM cells to bortezomib in single culture 3D collagen matrix. Patient 11 was a smoldering/standard-risk patient, and thus never previously treated with bortezomib. Patient 12 was a relapsed/standard-risk patient previously treated with bortezomib-based regimens, and high-dose melphalan followed by bone marrow transplantation. Patient 12's bortezomib-based induction regimen (bortezomib/lenalidomide/dexamethasone) occurred 3 years prior to the biopsy used for this in vitro assay. Patient 13 was a newly diagnosed/high-risk patient, while patient 17 was a smoldering myeloma patient.

Melphalan and bortezomib chemosensitivity among MM patients. FIG. 11 depicts the in vitro chemosensitivity of three MM patients to melphalan in single culture: patient 14, patient 11 (smoldering myeloma), and patient 12 (relapsed after bone marrow transplantation). The $EC_{50s}$ at 24 h exposure were 4 µM for patients 14 and 12, and 1 µM for patient 11. However, the percentage surviving cells at 20 µM, a more physiological concentration of high-dose melphalan treatment, was 30% for patient 12, 11% for patient 14, and 4% for patient 11. FIG. 12 represents bortezomib chemosensitivity of patients 11, 12, 13 (newly diagnosed) and 17 (smoldering myeloma). For patients 11 and 12, EC50 after 24 h continuous exposure was below 2 nM, however, at higher concentrations, MM cells from patient 11 were significantly more resistant: 30% live cells at 50 nM bortezomib for patient 11, and ~8% for patient 12. 24 h $EC_{50}$ for patient 13 was approximately 10 nM, while $EC_{50}$ was not reached with the sample from patient 17.

Figure 13:
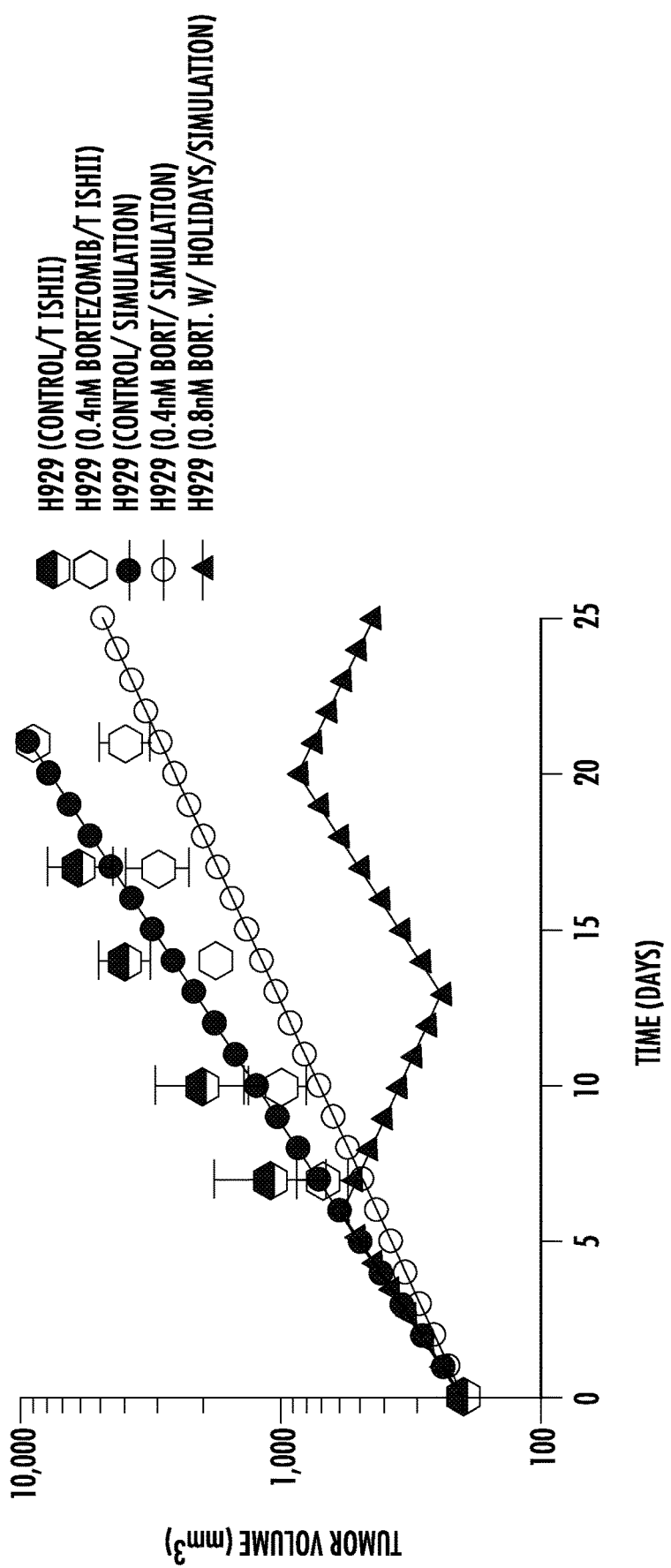
FIG. 13: Computational modeling of in vivo response to therapy. By parameterizing Equation 3 with the dose response constants obtained from NCI-H929 cells exposed to a bortezomib gradient (FIG. 2), it was possible to simulate how a bi-weekly treatment of a subcutaneous SCID mouse model would affect tumor growth. Pearson's correlation "r value" was 0.9869 (P=0.0003) between actual measurements (Ishii T, Seike T, et al. Blood Cancer J 2012; 2) and simulated tumor burden under a 1 mg/kg bi-weekly bortezomib regimen, which leads to a stable concentration of ~0.4 nM bortezomib in plasma (Williamson M J, Silva M D, et al. Mol Cancer Ther 2009; 8:3234-43). Using the same computational model, it was possible to test hypothetical treatments, such as, for instance, a regimen with holidays where the double of the amount of bortezomib would be administered every other week (0.8 nM w/holidays).
Figure 14:
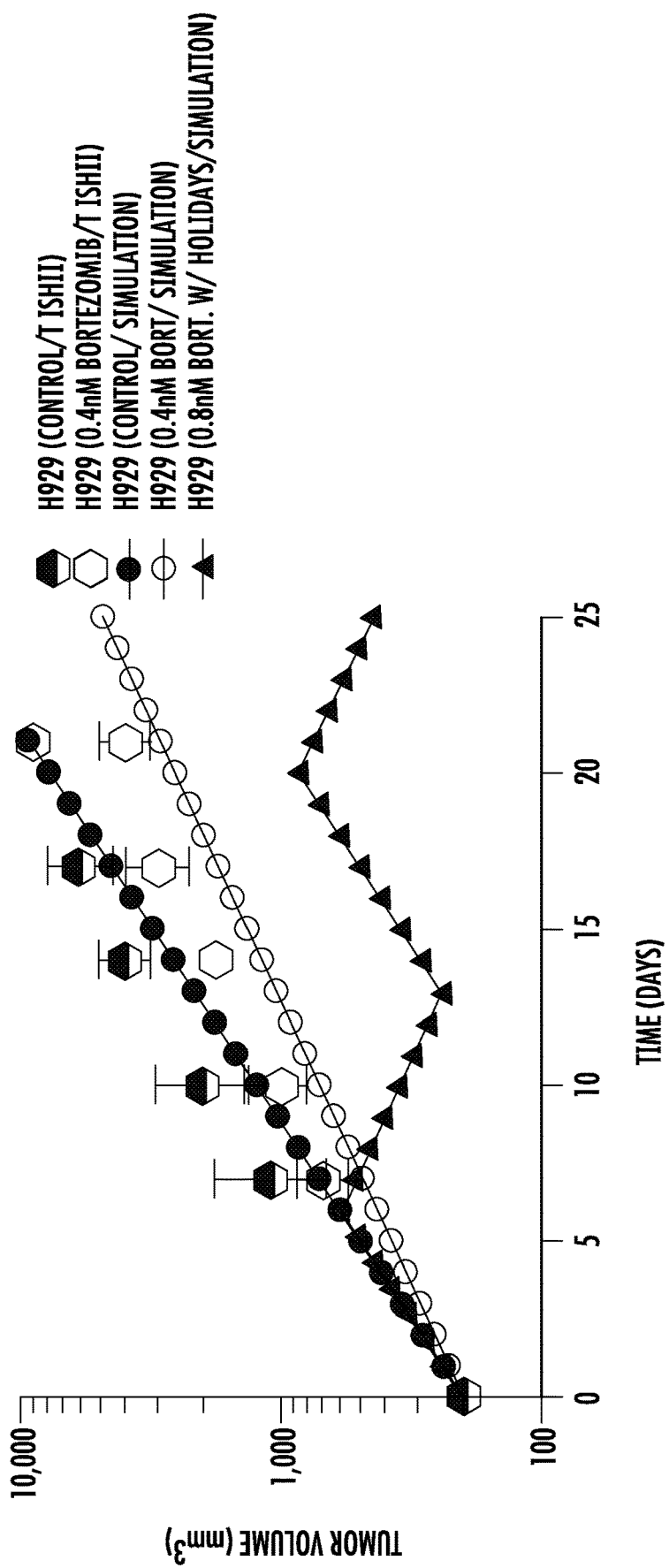
FIG. 14: Computational modeling of clinical response to therapy. The parameters of bortezomib chemosensitivity obtained in vitro from four patients (FIG. 7) were used in Equation 3 to simulate how these patients would have responded to a single agent bortezomib hypothetical treatment. The regimen simulated was 1.3 mg/m² doses on days 1, 4, 8, and 11, leading to a stable plasma concentration of approximately 1 nM (Reece D E, Sullivan D, et al. Chemother Pharmacol 2011; 67:57-67).

Extrapolation of in vitro data into in vivo and clinical response. By parameterizing Equation 3 with values obtained from fitting Equation 1 to the in vitro dose response data, it is possible to simulate how a tumor mass would respond to a therapeutic regimen. As an example, the sub-cutaneous mouse model SCID (severe combined immunodeficient), when implanted with the cell line NCI-H929, develops a tumor that grows 45-fold in 20 days (Nakashima T, Ishii T, et al. Clinical Cancer Research 2010; 16:2792-802). When treated with 1 mg/kg bortezomib twice a week, the tumor growth is reduced, and tumors are 20-fold bigger at day 20 than at implantation (Ishii T, Seike T, et al. Blood Cancer J 2012; 2). From the bortezomib in vitro chemosensitivity assay with the cell line NCI-H929 (FIG. 4), the parameters from Equation 3 were: IC50Rx=10.35 nM, IC50ΔT=10.38 h, expRX=2.7, and expT=7.1. FIG. 13 depicts the computational simulation of the tumor growth under control conditions, under a bi-weekly treatment with 1 mg/kg of bortezomib (which leads to a stable blood concentration of 0.4 nM (Williamson M J, Silva M D, et al. Mol Cancer Ther 2009; 8:3234-43)), and a hypothetical regimen where mice received a pulsed therapy with the same AUC (area under the curve), with bi-weekly injections of bortezomib every other week (therapy holidays). The simulated tumor would have increased 53.4-fold in control conditions (Pearson r=0.9762), 18-fold in standard bortezomib treatment (Pearson r=0.9869), and 5-fold in the hypothetical pulsed regimen. The same approach was used to simulate the response of patients 11, 12, 13, and 17 to a single agent regimen of bortezomib (1.3 mg/m², FIG. 14). In this regimen, plasma concentration stabilizes at approximately 1 nM (Reece D E, Sullivan D, et al. Chemother Pharmacol 2011; 67:57-67), and according to simulations, would achieve complete response in patients 11 an 12, relapse in patient 17, and no response in patient 13.

Discussion:

An interdisciplinary platform to study pre-clinical drug activity in primary MM cells has been described herein. First, MM cells were embedded in a microfluidic chamber that recapitulates the bone marrow microenvironment, including high cell density, extracellular matrix and patient-derived stromal cells. A linear and stable drug gradient was established across the chamber, which is then imaged sequentially in bright field. A digital image analysis algorithm detected live MM cells by the motion of cell membrane: upon death this activity ceases. The measurements of viability, at different concentrations and time points, were fit to mathematical models of chemosensitivity. These models can represent one or multiple sub-populations, and can be empirical or mechanistic. The data from these experiments can thus be used to parameterize mathematical models to simulate clinical outcome.

This platform overcomes some limitations of pre-clinical assays using primary cancer cells. It has been shown that extracellular matrix and stroma may be components of chemoresistance in many tumors. However, the inclusion of these elements significantly increases the complexity of dose response assays, often requiring the separation between cancer and stromal cells, by matrix digestion and/or flow sorting (Misund K, Baranowska K A, et al. J Biomol Screen 2013; 18:637-46). Also, viability assays are often destructive or cytotoxic, if carried for long periods of time, limiting the information acquired in the temporal dimension. In the disclosed assay, MM cells, stroma and matrix were never separated, and no cytotoxic agents were used to determine cell viability, thus allowing longitudinal studies of drug activity without interfering with the microenvironment.

In cancers such as MM, where a few million cells are obtainable per patient biopsy, it is important to minimize the number of cells per experimental condition, which was in the order of 1,000-10,000 cells in this assay. The poor clonal efficiency of MM cells, as well as their spontaneous death in vitro (Suggitt M, Bibby M C. Clinical Cancer Research 2005; 11:971-81), suggest that experiments with these samples be performed in the first few days after the biopsy. By studying the effect of long-term exposure and drug withdrawal in human MM cell lines, mechanistic theoretical models of the drug activity were created (Gardner S N. Cancer Res 2000; 60:1417-25). Once a model is generated for a particular drug, the data from patient samples can be used to parameterize and extrapolate the response for longer periods of time.

As shown for bortezomib-induced melphalan sensitization in co-culture (FIG. 6), this system can be used to study drug interactions (Chou T C. Pharmacol Rev 2006; 58:621-81). The addition of the time dimension, instead of fixed time points, would allow the study of time-shifted drug combinations, such as, for instance, nuclear export agents and doxorubicin (Turner J G, Marchion D C, et al. Cancer Res 2009; 69:6899-905). Combination indices (Chou T C. Pharmacol Rev 2006; 58:621-81) may be obtained by adding the two drugs being studied on the same reservoir, which will induce two superimposed drug gradients.

This assay allows the observation of individual cells. Thus, it is possible to assess the heterogeneity of drug response by plotting in a histogram the area under the curve (AUC) at the moment of death of each individual cell. Further improvements in the digital image analysis algorithm could identify and track individual cells, from their original replication until their death. By combining this information with the dose response surfaces, it would be possible to determine if particular drugs and concentrations are capable of maintaining a tumor burden quiescent, or in a balance between proliferation and death (Wells A, Griffith L, et al. Cancer Res 2013; 73:3811-6; San-Miguel J F, Mateos M V. Haematol-Hematol J 2011; 96:1246-8).

These results describe a framework to better understand the dynamics of interactions between tumor and stroma in response to therapeutic agents in vitro. These assays can be performed in a middle- to high-throughput manner, and significantly reduce the complexity of working with patient primary cells in reconstructions of the tumor microenvironment. This can become a platform for personalized preclinical estimation of drug efficacy in cancer.

Example 2

Figure 15:
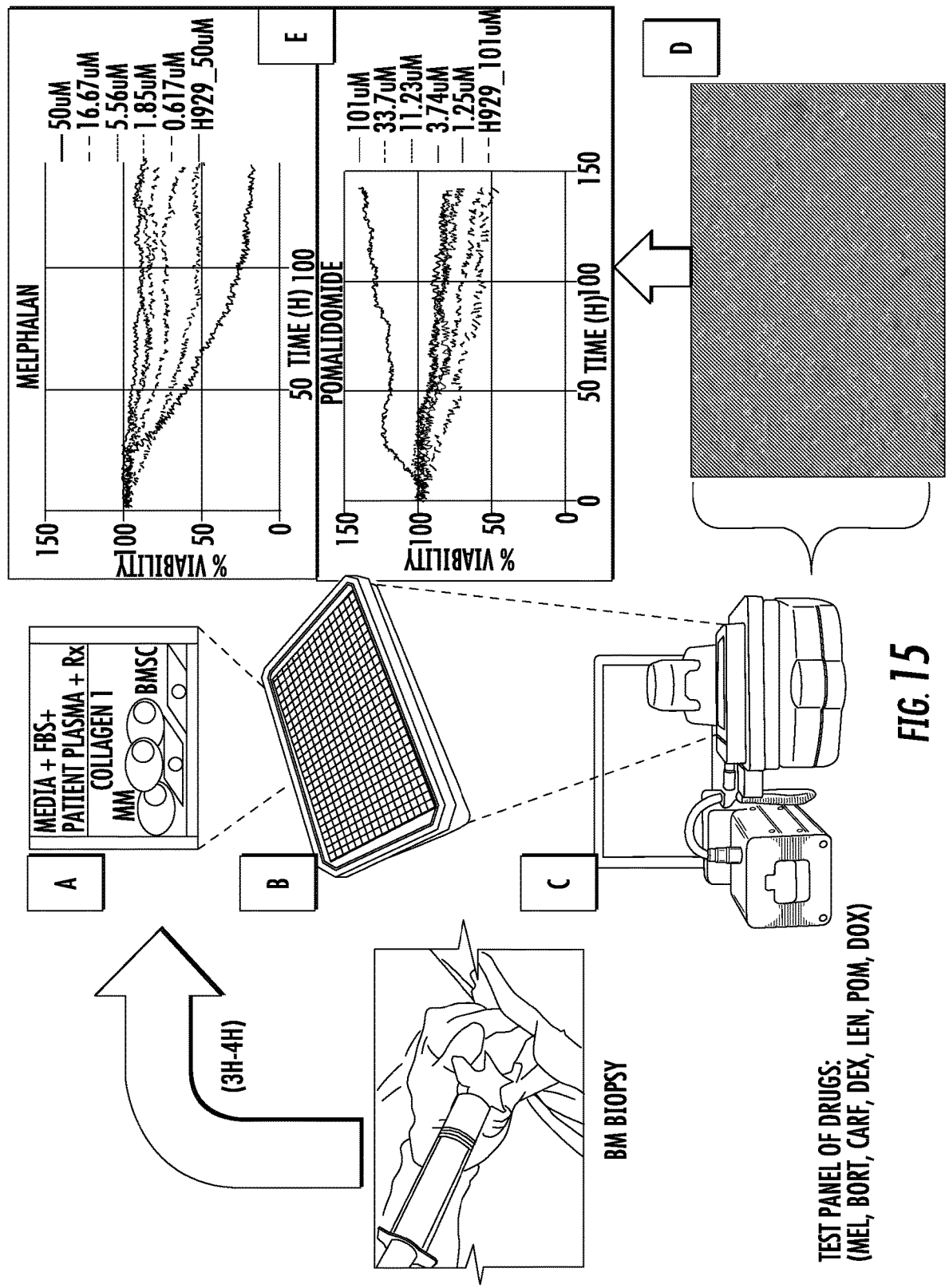
FIG. 15: Schematic view of multiwell assay. During a standard-of-care bone marrow biopsy, an extra volume of 10 mL of aspirate was taken for research. The cancer cells were separated from non-cancer by magnetic bead sorting (antibody for CD138, a marker of MM cells). Cancer cells from the patient were re-suspended in collagen I or matrigel or any other matrix of choice in conjunction with stromal cells (adherent non-cancer cells obtained from bone marrow biopsies, CD138−) (A). This cell-matrix mix was seeded in multi-well plates and left to polymerize overnight. During this process the stromal cells adhere to the bottom of the wells while MM cells remain in suspension (B). The wells are organized so that multiple drugs can be tested, each at a number of different concentrations (e.g., 5) and in different number of replicates (e.g., 2 or more). By imaging at regular intervals each well in bright field, and using a digital image analysis algorithm (FC), live and dead cells were detected non-destructively at each well (D). The replicates were then combined and the results for each drug were clustered, normalized by the controls (no drugs added) and the dose-response curves were built (E).

During a standard-of-care bone marrow biopsy, an extra volume of 10 mL of aspirate was taken for research. The cancer cells were separated from non-cancer by magnetic bead sorting (antibody for CD138, a marker of MM cells). Cancer cells from the patient were re-suspended in colagen I or matrigel or any other matrix of choice in conjunction with stromal cells (adherent non-cancer cells obtained from bone marrow biopsies, CD138−) (FIG. 15A). This cell-matrix mix was seeded in multi-well plates and left to polymerize overnight. During this process the stromal cells adhere to the bottom of the wells while MM cells remain in suspension (FIG. 15B). The wells are organized so that multiple drugs can be tested, each at a number of different concentrations (e.g., 5) and in different number of replicates (e.g., 2 or more) (e.g., FIG. 16). By imaging at regular intervals each well in bright field, and using a digital image analysis algorithm (FIG. 15C), live and dead cells were detected non-destructively at each well (FIG. 15D). The replicates were then combined and the results for each drug were clustered, normalized by the controls (no drugs added) and the dose-response curves were built (FIG. 15E).

FIG. 16 displays a schematic of an example multiwell plate used to run multiple experiments. One sample from a patient (wells in columns 2-8 and rows B-L) was tested for sensitivity to 7 drugs: melphalan (MEL), carfilzomib (CFZ), dexamethasone (DEX), doxorubicin (a.k.a. Adriamycin, ADR), Selinexor (KPT), Panobinostat (PAN) and Quisinostat (QST). The highest concentrations of drug were on row 'B' and are serially diluted 3-fold every row from 'C' to 'F', thus 5 different drug concentrations for each drug. The same pattern was repeated from line 'H' until 'L', representing the second replicate. Squares 114-117 represent the controls: the cells in these wells did not receive any drug. The concentrations in row 'M' are the highest concentration for each drug in the panel. In the same plate, a second experiment was performed to assess how the microenvironment can affect drug efficacy. For this experiment, a multiple myeloma cell line in co-culture with mesenchymal stem cells in collagen matrix (columns 10-16, rows B-E and columns 11 and 12 on row G), in single culture in collagen matrix (columns 12, 13, 20, and 21 on row G, and columns 10-16 and 18-24 on rows H-L) and in single culture in media (Columns 18-24, rows B-F, and columns 18 and 19 on row G) were used.

Figure 17:
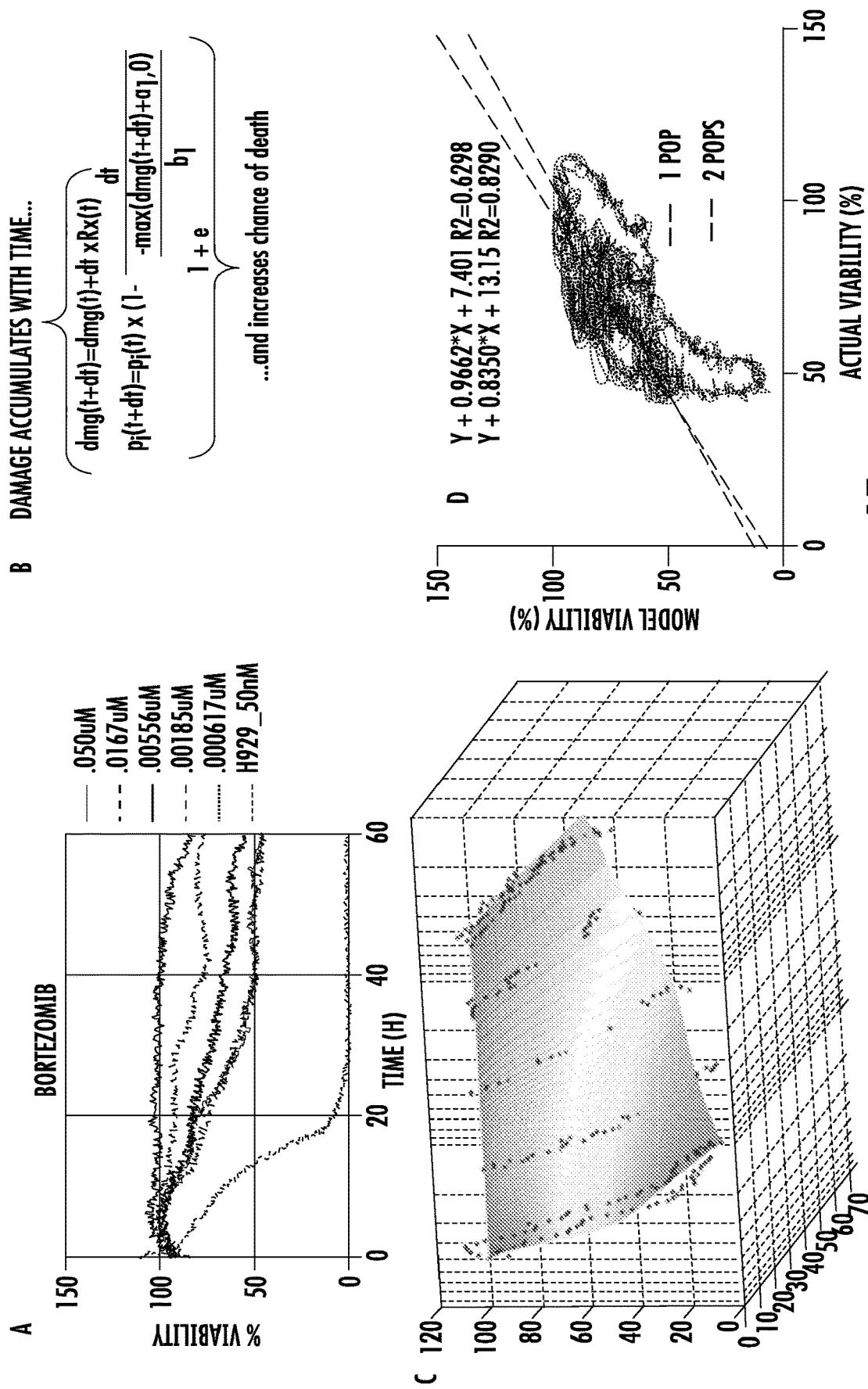
FIG. 17: Example of the model implementation. (A) The dose-response curves for each patient and each drug were fit to (B) a computational model that describes the rate of accumulation of damage due to drug exposure as well as drug-induced cell death due to accumulated damage. The patient-specific model can be represented by one population (perfectly homogeneous tumor), two populations or three populations. (C and D) Pearson's correlation of these three hypotheses were computed, and the model with fewest populations and best fit (highest $r^2$) was selected.
Figure 18:
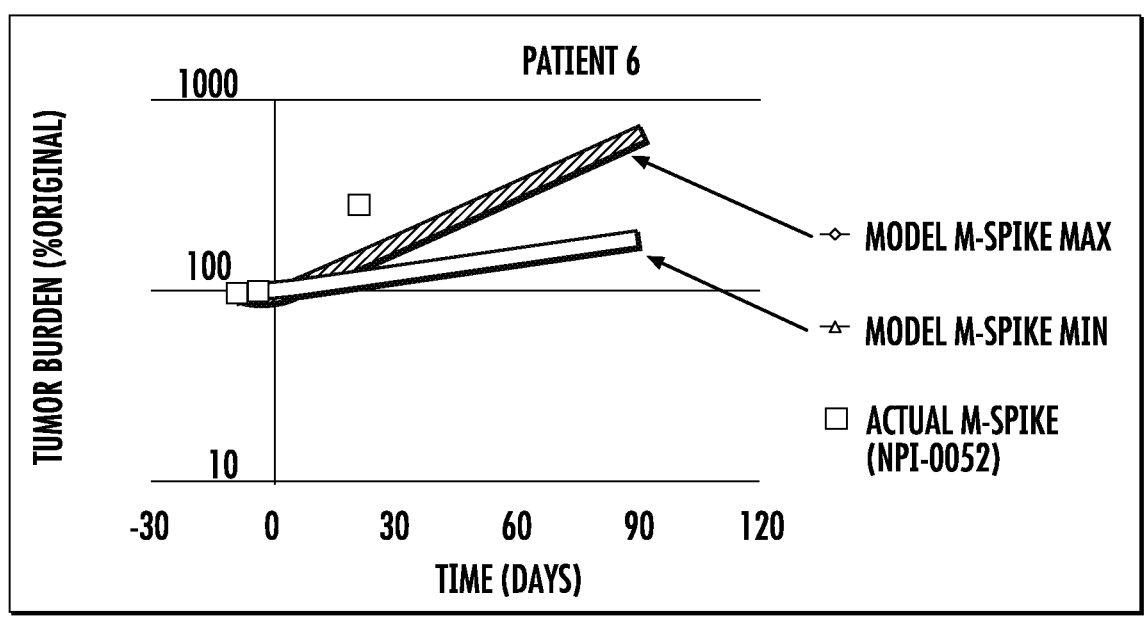
FIG. 18: Dose-response curve for Patient 6 and Marizomib (NPI-0052). A selected patent-specific model was simulated in a clinical regimen of the drug, and two estimates are made: "best case" scenario (Model M-Spike Max) and "worst case" scenario (Model M-Spike Min). In the "worst case" scenario the growth rate is 1% for newly diagnosed patients and the highest previous growth rate of the tumor for relapsed patients, based on prior clinical data. In the "best case" scenario the growth rate of the tumor is zero for newly diagnosed patients and the minimum between 1% and "worst case" rate for relapsed patients.
Figure 19:
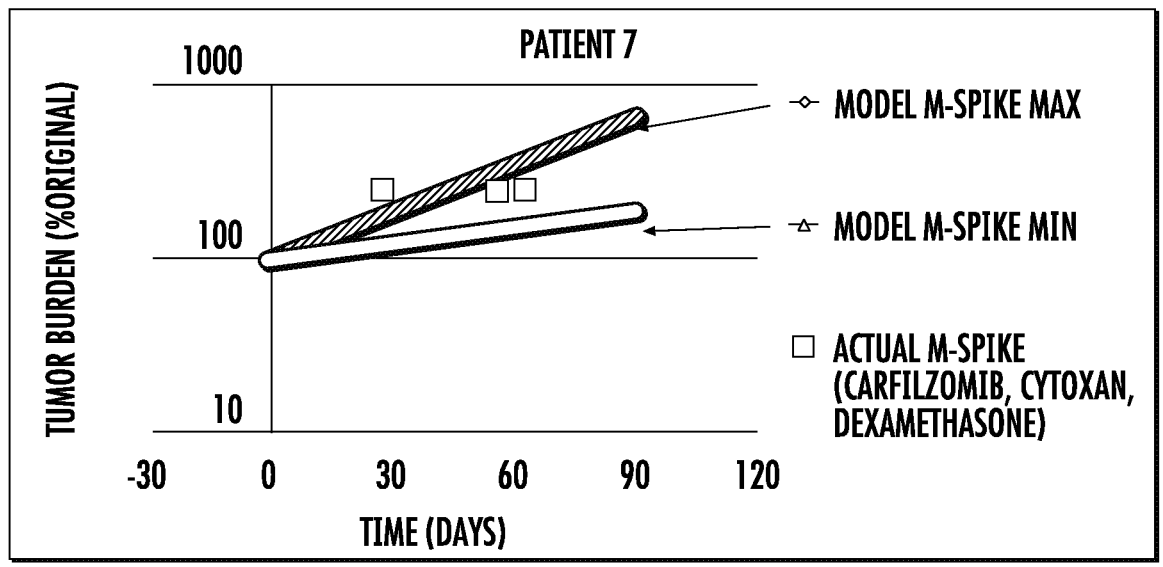
FIG. 19: Dose-response curve for Patient 7 and a drug combination of Carfilzomib, Cytoxan and Dexamethasone. A selected patent-specific model was simulated in a clinical regimen of the drug, and two estimates are made: "best case" scenario (Model M-Spike Max) and "worst case" scenario (Model M-Spike Min). In the "worst case" scenario the growth rate is 1% for newly diagnosed patients and the highest previous growth rate of the tumor for relapsed patients, based on prior clinical data. In the "best case" scenario the growth rate of the tumor is zero for newly diagnosed patients and the minimum between 1% and "worst case" rate for relapsed patients.
Figure 20:
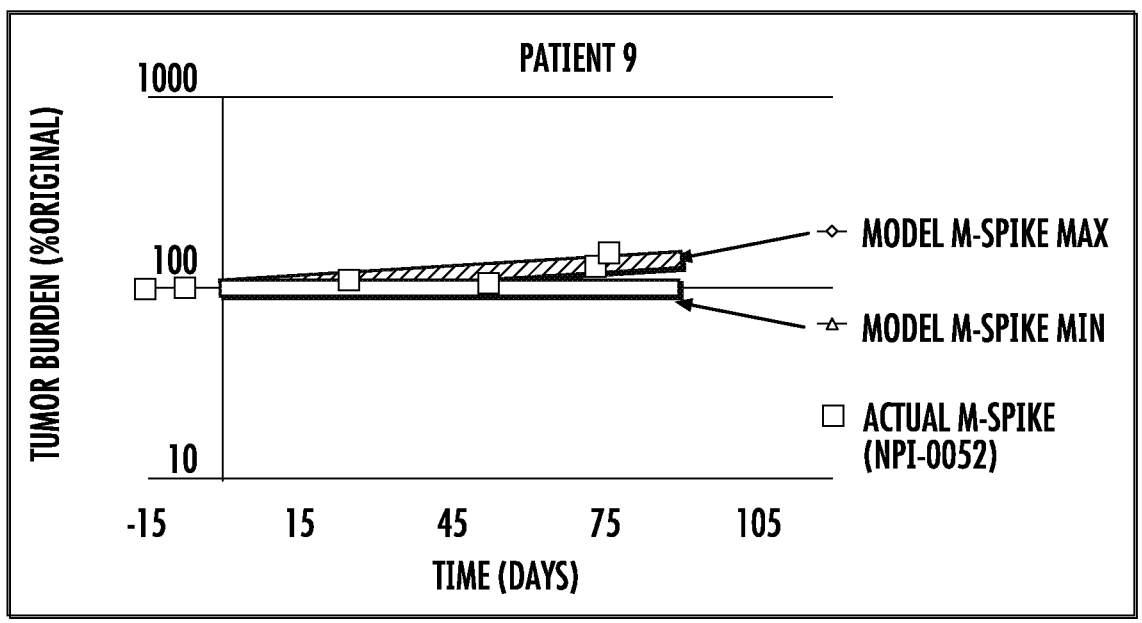
FIG. 20: Dose-response curve for Patient 9 and Marizomib (NPI-0052). A selected patent-specific model was simulated in a clinical regimen of the drug, and two estimates are made: "best case" scenario (Model M-Spike Max) and "worst case" scenario (Model M-Spike Min). In the "worst case" scenario the growth rate is 1% for newly diagnosed patients and the highest previous growth rate of the tumor for relapsed patients, based on prior clinical data. In the "best case" scenario the growth rate of the tumor is zero for newly diagnosed patients and the minimum between 1% and "worst case" rate for relapsed patients.
Figure 21:
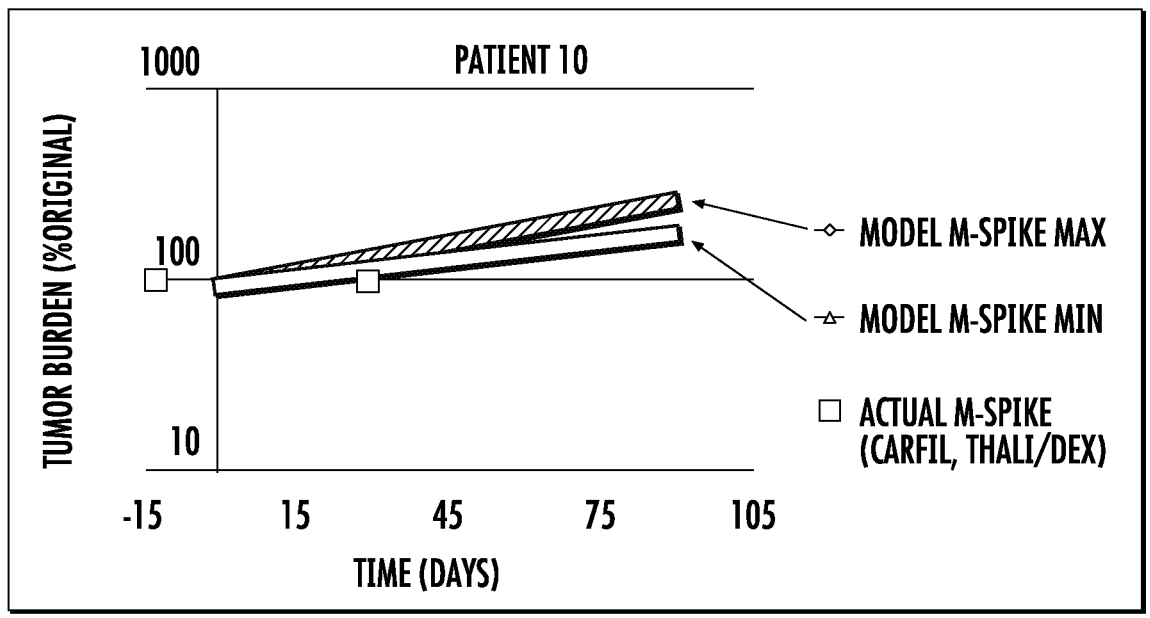
FIG. 21: Dose-response curve for Patient 10 and a drug combination of Carfilzomib, Thalidomide (Thali), and Dexamethasone. A selected patent-specific model was simulated in a clinical regimen of the drug, and two estimates are made: "best case" scenario (Model M-Spike Max) and "worst case" scenario (Model M-Spike Min). In the "worst case" scenario the growth rate is 1% for newly diagnosed patients and the highest previous growth rate of the tumor for relapsed patients, based on prior clinical data. In the "best case" scenario the growth rate of the tumor is zero for newly diagnosed patients and the minimum between 1% and "worst case" rate for relapsed patients.
Figure 22:
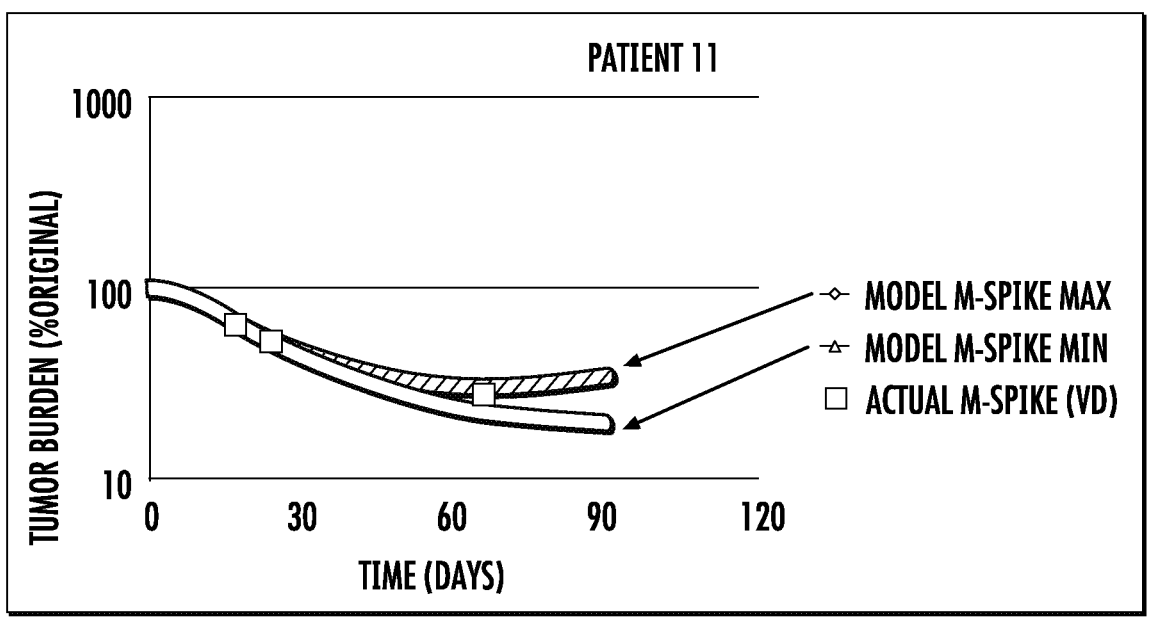
FIG. 22: Dose-response curve for Patient 11 and a drug combination of Bortezomib (V) and Dexamethasone (D). A selected patent-specific model was simulated in a clinical regimen of the drug, and two estimates are made: "best case" scenario (Model M-Spike Max) and "worst case" scenario (Model M-Spike Min). In the "worst case" scenario the growth rate is 1% for newly diagnosed patients and the highest previous growth rate of the tumor for relapsed patients, based on prior clinical data. In the "best case" scenario the growth rate of the tumor is zero for newly diagnosed patients and the minimum between 1% and "worst case" rate for relapsed patients.
Figure 23:
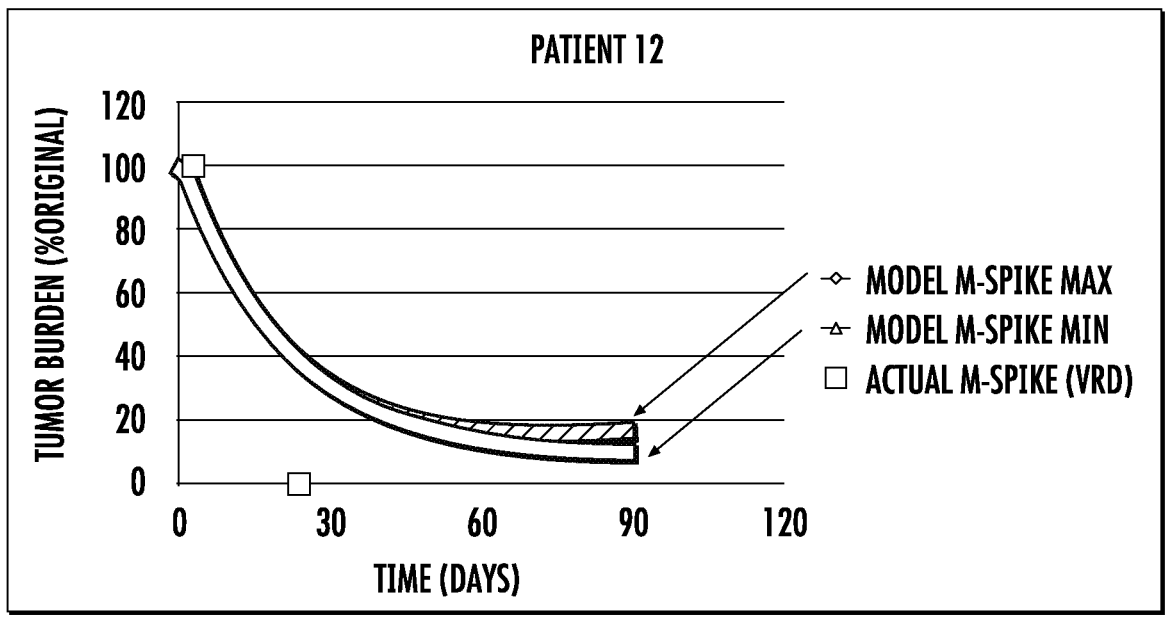
FIG. 23: Dose-response curve for Patient 12 and a drug combination of Bortezomib (V), Lenalidomide (R), and Dexamethasone (D). A selected patent-specific model was simulated in a clinical regimen of the drug, and two estimates are made: "best case" scenario (Model M-Spike Max) and "worst case" scenario (Model M-Spike Min). In the "worst case" scenario the growth rate is 1% for newly diagnosed patients and the highest previous growth rate of the tumor for relapsed patients, based on prior clinical data. In the "best case" scenario the growth rate of the tumor is zero for newly diagnosed patients and the minimum between 1% and "worst case" rate for relapsed patients.
Figure 24:
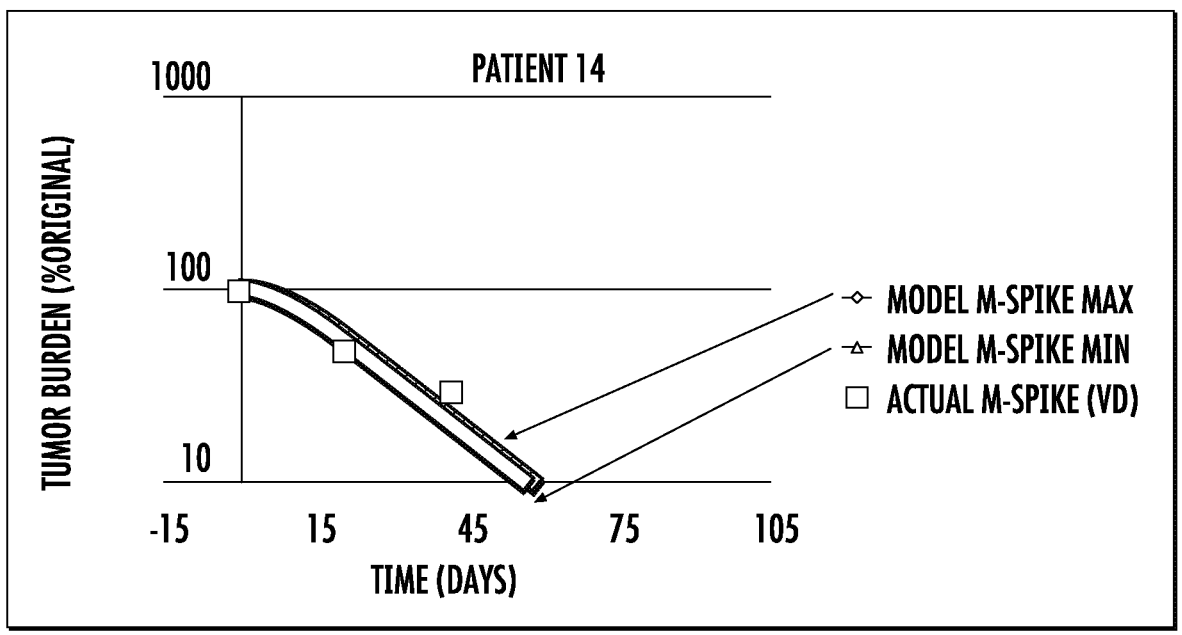
FIG. 24: Dose-response curve for Patient 14 and a drug combination of Bortezomib (V) and Dexamethasone (D). A selected patent-specific model was simulated in a clinical regimen of the drug, and two estimates are made: "best case" scenario (Model M-Spike Max) and "worst case" scenario (Model M-Spike Min). In the "worst case" scenario the growth rate is 1% for newly diagnosed patients and the highest previous growth rate of the tumor for relapsed patients, based on prior clinical data. In the "best case" scenario the growth rate of the tumor is zero for newly diagnosed patients and the minimum between 1% and "worst case" rate for relapsed patients.
Figure 25:
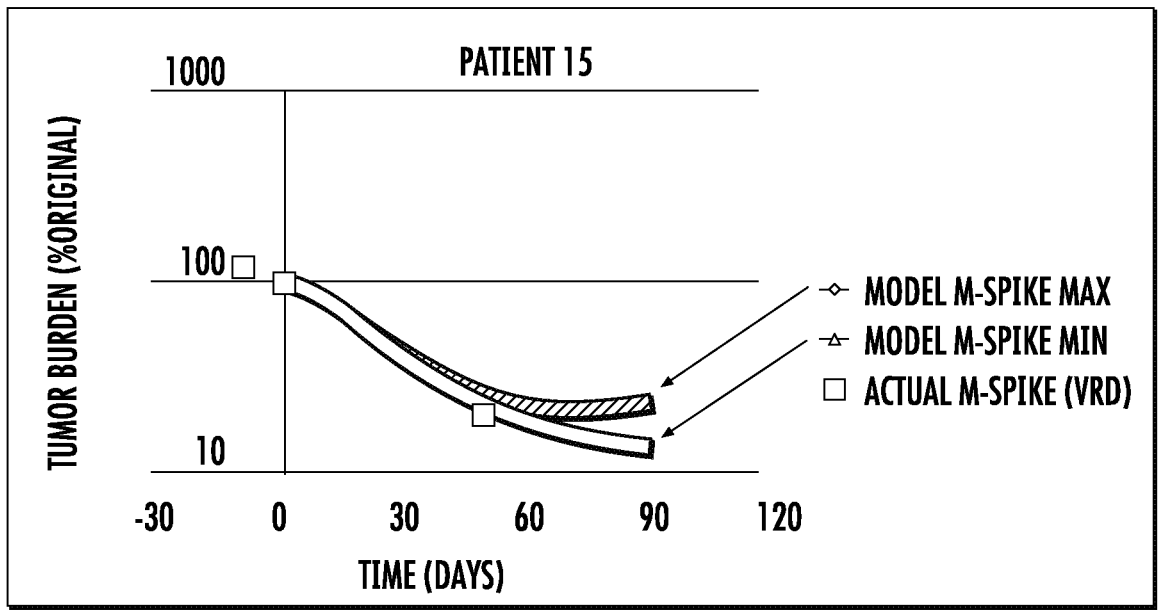
FIG. 25: Dose-response curve for Patient 15 and a drug combination of Bortezomib (V), Lenalidomide (R), and Dexamethasone (D). A selected patent-specific model was simulated in a clinical regimen of the drug, and two estimates are made: "best case" scenario (Model M-Spike Max) and "worst case" scenario (Model M-Spike Min). In the "worst case" scenario the growth rate is 1% for newly diagnosed patients and the highest previous growth rate of the tumor for relapsed patients, based on prior clinical data. In the "best case" scenario the growth rate of the tumor is zero for newly diagnosed patients and the minimum between 1% and "worst case" rate for relapsed patients.
Figure 26:
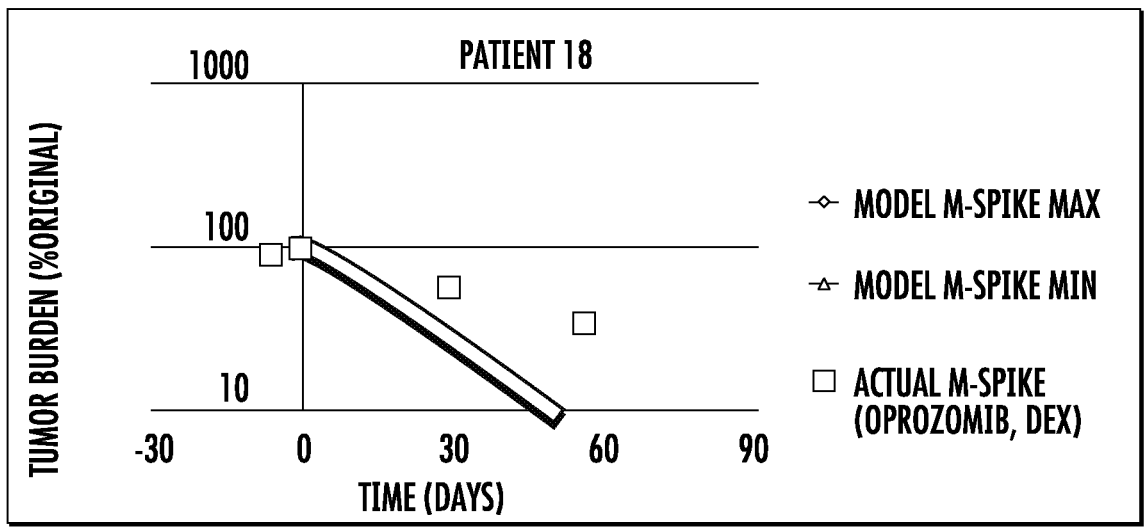
FIG. 26: Dose-response curve for Patient 18 and a drug combination of Oprozomib and Dexamethasone. A selected patent-specific model was simulated in a clinical regimen of the drug, and two estimates are made: "best case" scenario (Model M-Spike Max) and "worst case" scenario (Model M-Spike Min). In the "worst case" scenario the growth rate is 1% for newly diagnosed patients and the highest previous growth rate of the tumor for relapsed patients, based on prior clinical data. In the "best case" scenario the growth rate of the tumor is zero for newly diagnosed patients and the minimum between 1% and "worst case" rate for relapsed patients.
Figure 27:
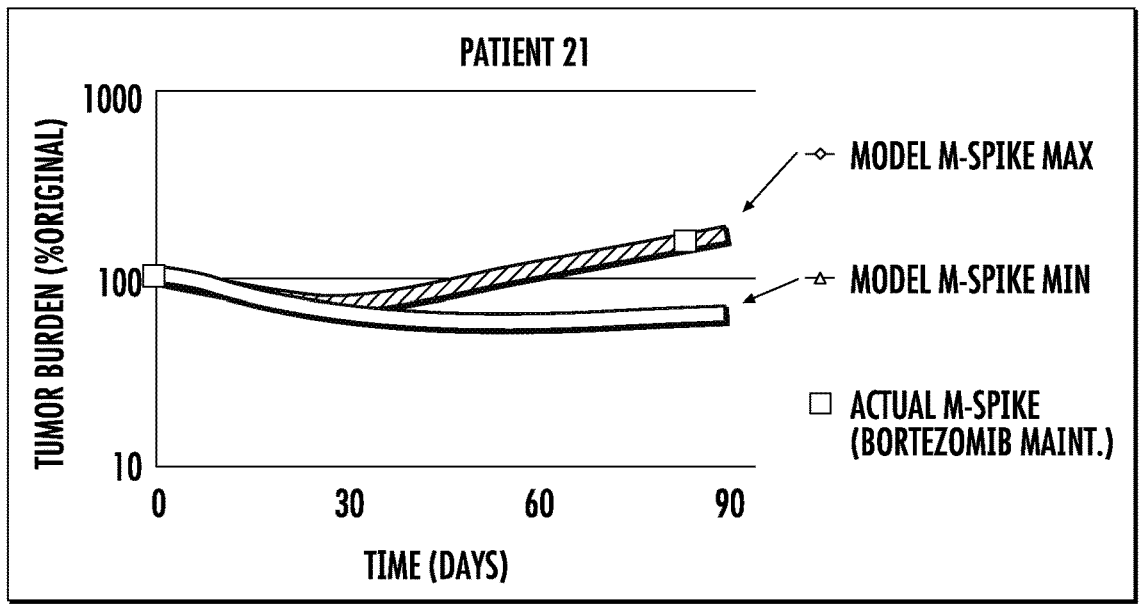
FIG. 27: Dose-response curve for Patient 21 and Bortezomib. A selected patent-specific model was simulated in a clinical regimen of the drug, and two estimates are made: "best case" scenario (Model M-Spike Max) and "worst case" scenario (Model M-Spike Min). In the "worst case" scenario the growth rate is 1% for newly diagnosed patients and the highest previous growth rate of the tumor for relapsed patients, based on prior clinical data. In the "best case" scenario the growth rate of the tumor is zero for newly diagnosed patients and the minimum between 1% and "worst case" rate for relapsed patients.

The dose-response curves for each patient and each drug (FIG. 17A) were fit to a computational model that describes the rate of accumulation of damage due to drug exposure as well as drug-induced cell death due to accumulated damage (FIG. 17B). The patient-specific model can be represented by one population (e.g., a perfectly homogeneous tumor), two populations or three populations. For instance, if only one population, then the tumor burden will be equal to p1(t); if two populations, then p1(t)+p2(t); and if three populations, p1(t)+p2(t)+p3(t). Each of these populations can be characterized by a set of parameters of chemosensitivity to a particular drug or drug combination, as described in the second equation in (FIG. 17B), namely $a_i$ and $b_i$. Thus for one population there are two parameters for the model to be fit, $a_1$ and $b_1$; for two populations there are 5 parameters, $a_1$, $a_2$, $b_1$, $b_2$, and $s_0$, which is the percentage of the second population at time of biopsy; for three populations there are 8 parameters: $a_1$, $a_2$, $a_3$, $b_1$, $b_2$, $b_3$, $s_0$ and $s_1$, which represent sensitivity parameters of the three populations plus the percentage at time of biopsy of the second and third populations. A Pearson correlation of these three hypotheses was used to choose the one with fewest populations and best fit (highest $r^2$) (FIG. 17D). The selected model was then simulated in a clinical regimen of the drug (FIGS. 18-27), and two estimates are made: "best case" (Model M-Spike Max in FIGS. 18-27) scenario and "worst case" (Model M-Spike Min in FIGS. 18-27) scenarios. In the "worst case" scenario the growth rate is 1% for newly diagnosed patients and the highest previous growth rate of the tumor for relapsed patients, based on prior clinical data. In the "best case" scenario the growth rate of the tumor is zero for newly diagnosed patients and the minimum between 1% and "worst case" rate for relapsed patients.

Figure 28:
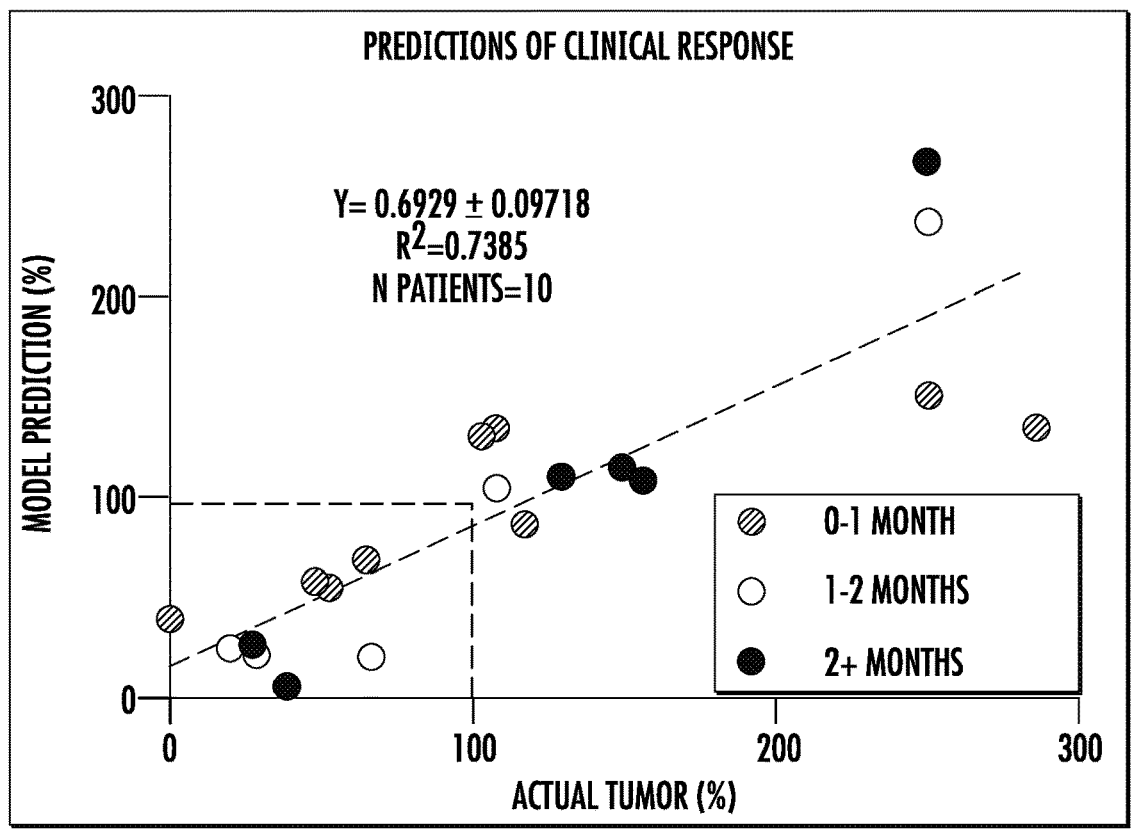
FIG. 28: Pearson correlation between actual and model predictions for normalized tumor burden measurements for 10 MM patients treated with proteasome inhibitor-based regimens at Moffitt Cancer Center. The dashed square shows that all patients for whom the model predicted a clinical response, actually responded, and all those predicted not to have a response indeed did not respond. Different filled in circles represent the interval of time after biopsy when each tumor measurement of made: less than a month (light grey), between one and two months (white), and over two months (dark grey).

FIG. 28 displays the Pearson correlation between actual and model predictions for normalized tumor burden measurements for 10 MM patients treated with proteasome inhibitor-based regimens at Moffitt Cancer Center. The dashed square shows that all patients for whom the model predicted a clinical response, actually responded, and all those predicted not to have a response indeed did not respond. Different filled in circles represent the interval of time after biopsy when each tumor measurement of made: less than a month (light grey), between one and two months (white), and over two months (dark grey).

FIG. 29 displays the actual and estimated normalized tumor burden for multiple myeloma patients treated in proteasome inhibitor-based regimens. 10 multiple myeloma patients who donated bone marrow aspirates for the assay described herein were followed after treatment. Each entry in the column 'Time (months)' represents the delay (in months) between the tumor burden measurement and the original biopsy. Column 'Clinical Burden (% original)' represents the tumor burden measurement at that particular moment in time normalized by the tumor burden at the time of biopsy. 'Mean' is the average between the model estimations for best ('Min') and worst ('Max') case scenarios, which correspond to smallest and largest tumor estimation. 'Treatment' represents the actual clinical treatment received by the patient. 'Drug Ex vivo' represents the drug used to test the sensitivity of the cells of these patients and create the estimations of clinical response. While these patients have been tested ex vivo for one particular proteasome inhibitor (bortezomib), these models were able to reliably estimate clinical response of patients treated with different proteasome inhibitor drugs as single agents (phase I trials) or in combination with other drugs (IMIDS).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A non-destructive method for assessing primary cancer cell viability following contact with an active agent said method comprising
   (a) culturing a plurality of primary cancer cells from a subject in a chamber;
   (b) contacting the primary cancer cells in the chamber with an active agent;
   (c) capturing a first bright field image from the primary cancer cells contacted with the active agent at a first time point;
   (d) capturing a second bright field image from the primary cancer cells contacted with the active agent at a second time point; wherein the capture of the first and second bright field images does not destroy the primary cancer cells providing for longitudinal analysis; wherein the longitudinal analysis provides data for at least 2 days; and
   (e) detecting cell membrane motion of the primary cancer cells between the first and second time points; wherein cell membrane motion is detected by stacking the first and second bright field images, subtracting background, aligning the images whereby translational motion caused by vibration and movement of the chamber is removed, detecting maximal pixel intensity across the images, thereby forming a maximal pixel intensity image, and subtracting the first bright field image from the maximal pixel intensity image; wherein an image remaining following the first optical image being subtracted from the maximal pixel intensity image indicates membrane motion; and wherein presence of membrane motion indicates a viable primary cancer cell and absence of motion indicates primary cancer cell death.

2. The method of claim 1, further comprising collecting parameters to generate a multi-parameter model that summarizes the response of the subject to the active agent.

3. The method claim 1, further comprising selecting a cancer treatment regimen for the subject based on the results of the multi-parameter model.

4. The method of claim 1, wherein the cancer comprises a hematological cancer.

5. The method of claim 1, wherein the cancer comprises multiple myeloma.

6. The method of claim 1, wherein the chamber recapitulates the cancer microenvironment.

7. The method of claim 1, wherein the chamber comprises extracellular matrix, subject-derived stroma, and growth factors to recapitulate the cancer microenvironment.

8. The method of claim 1, wherein the chamber comprises a microfluidic chamber.

9. The method of claim 1, wherein the chamber comprises a well in a multiwell-plate.

10. The method of claim 1, further comprising collecting a sample from the subject and isolating the cells from the sample.

11. The method of claim 10, wherein the sample comprises a bone marrow aspirate.

12. The method of claim 1, wherein the active agent comprises an anticancer agent.

13. The method of claim 1, wherein the active agent comprises a combination of active agents.

14. The method of claim 1, further comprising preparing a three-dimensional dose-response curve by assaying the viability of cells from the subject in response to the active agent at a plurality of time points at a plurality of dosages; wherein the method indicates an effective dosing schedule of the active agent.

15. The method of claim 1, wherein method indicates an effective concentration of the active agent.

16. The method of claim 1, wherein the active agent comprises, melphalan, bortezomib, FAM-HYD-1, Marizomib (NPI-0052), Carfilzomib, Cytoxan, Dexamethasone, Thalidomide, Lenalidomide, Oprozomib, Panobinostat, Quisinostat, Selinexor, or a combination thereof.

* * * * *